(12) United States Patent
Johnson et al.

(10) Patent No.: US 7,901,450 B2
(45) Date of Patent: *Mar. 8, 2011

(54) VASCULAR ANCHORING SYSTEM AND METHOD

(75) Inventors: Timothy Johnson, Bothell, WA (US); George W. Keilman, Bothell, WA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/048,063

(22) Filed: Mar. 13, 2008

(65) Prior Publication Data

US 2009/0234434 A1    Sep. 17, 2009

(51) Int. Cl.
*A61F 2/06* (2006.01)
(52) U.S. Cl. .................................... 623/1.35; 623/1.36
(58) Field of Classification Search ................. 623/1.35
See application file for complete search history.

(56) References Cited

U.S. PATENT DOCUMENTS

2005/0137450 A1*  6/2005  Aronson et al. ............... 600/37
2005/0177224 A1*  8/2005  Fogarty et al. ............ 623/1.35

* cited by examiner

*Primary Examiner* — David Isabella
*Assistant Examiner* — Jacqueline Woznicki

(57) ABSTRACT

As described herein, vascular anchoring systems are used to position an implant in a vascular area such as a bifurcated vasculature with relatively high fluid flow, for instance, in an area of a pulmonary artery with associated left and right pulmonary arteries. Implementations include an anchoring trunk member having a first anchoring trunk section and a second anchoring trunk section. Further implementations include a first anchoring branch member extending from the anchoring trunk member. Still further implementations include a second anchoring branch member extending from the anchoring trunk member.

18 Claims, 45 Drawing Sheets

VASCULAR ANCHORING SYSTEM AND METHOD

BACKGROUND OF THE INVENTION

1. Field of the Invention

The present invention is directed generally to implant systems.

2. Description of the Related Art

For an implant system sized for insertion within a vascular area there are challenges in positioning and maintaining the implant in a desired location within the vascular area. These challenges can be further increased when the implant is sectioned into portions that need to be positioned relative to one another. Unintended movement of such portions, such as near or inside a heart organ, can lead to misalignment or undesired consequences.

BRIEF DESCRIPTION OF THE SEVERAL VIEWS OF THE DRAWING(S)

Figure 1:
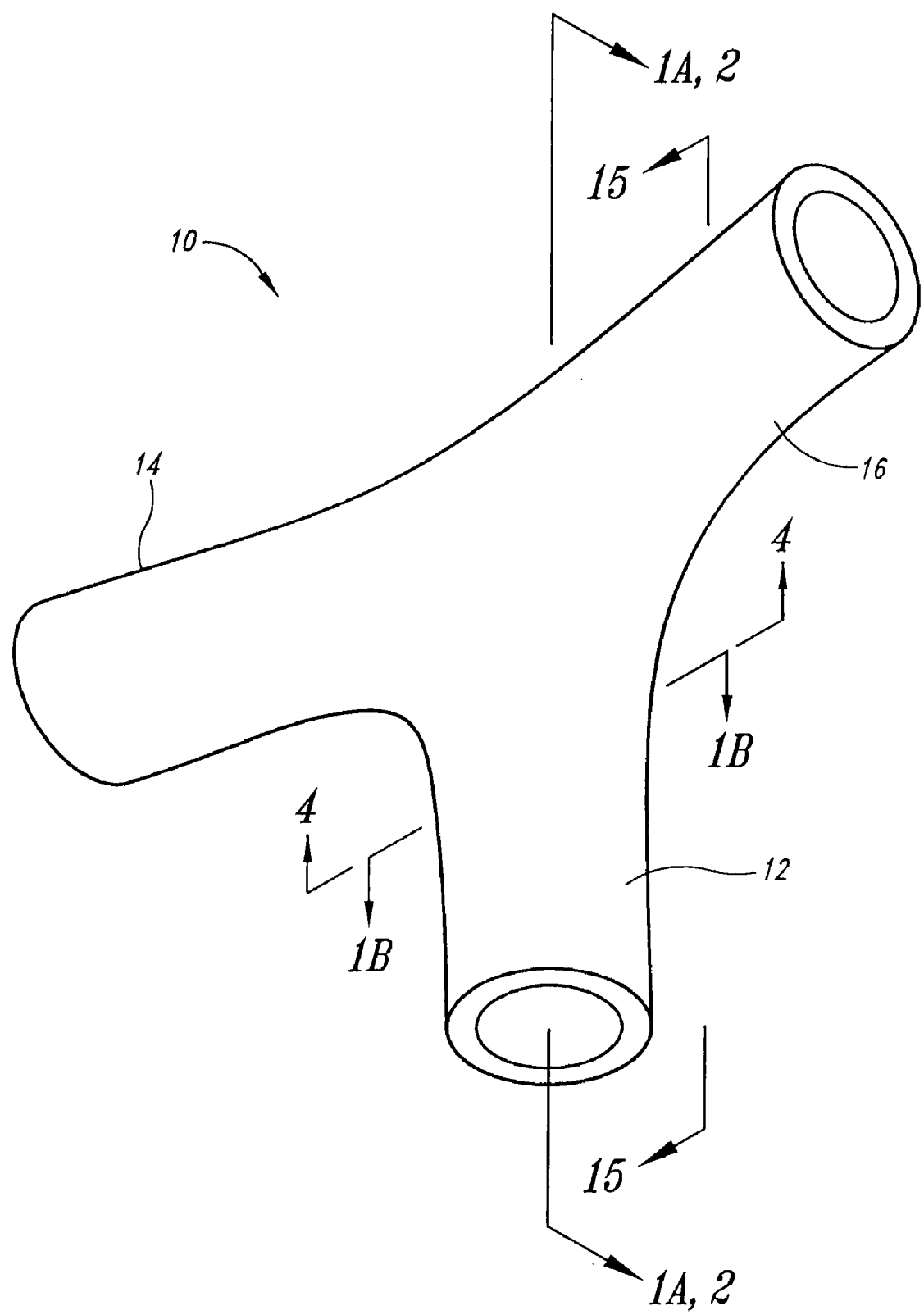
FIG. 1 is a perspective-fragmented view of an exemplary vascular area depicted as a bifurcated vasculature to receive a vascular anchoring system disclosed herein.
Figure 30:
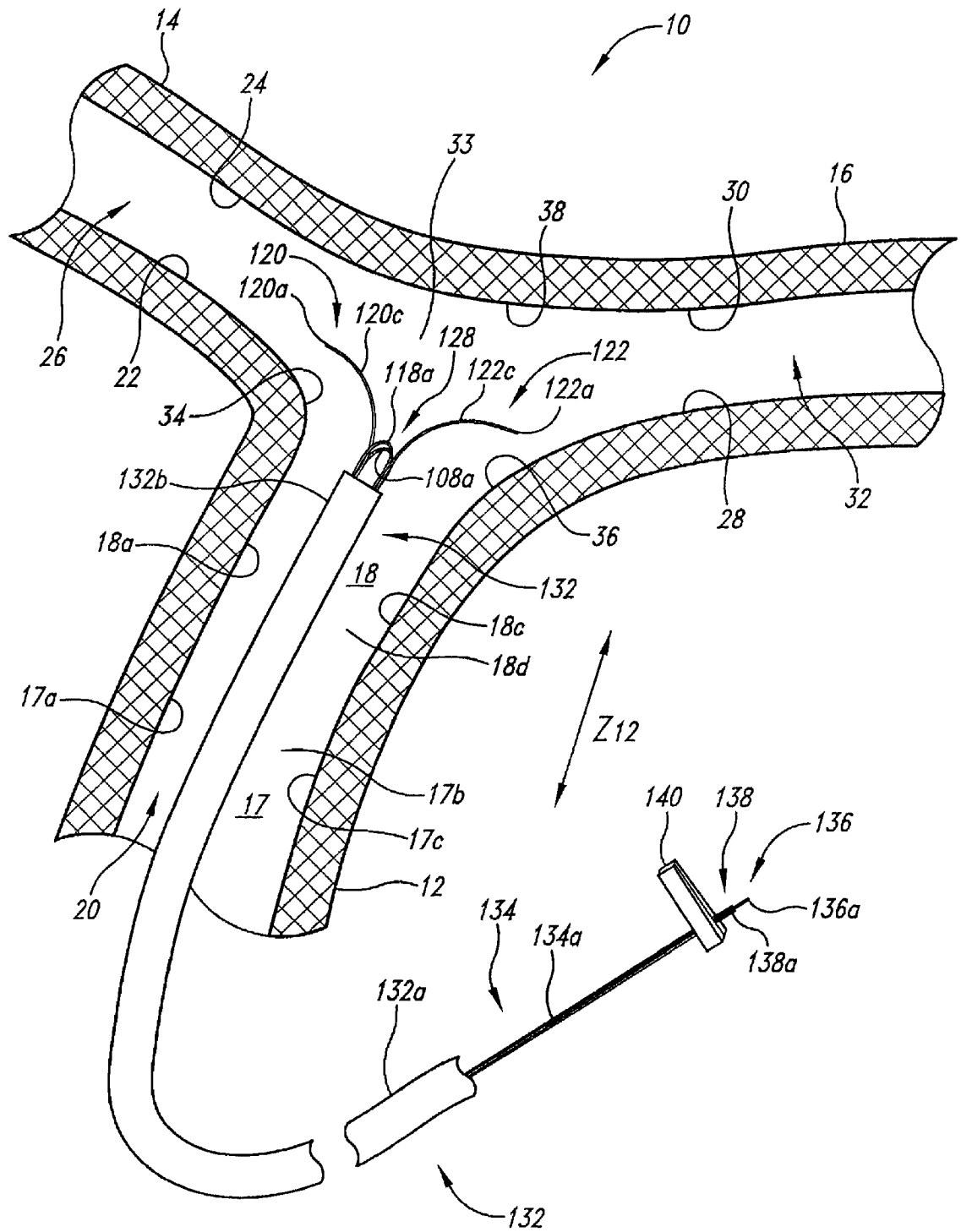

FIG. 30 is a sectional fragmented view of the bifurcated vasculature of FIG. 1 taken along the 1A-1A line and a front elevational fragmented view of the second catheter end inserted into the vascular trunk with a portion of the third vascular anchoring system extending therefrom by a first amount and the first catheter end external to the bifurcated vasculature with the first end of the deployment tether extending therefrom by a first diminished amount.

Figure 31:
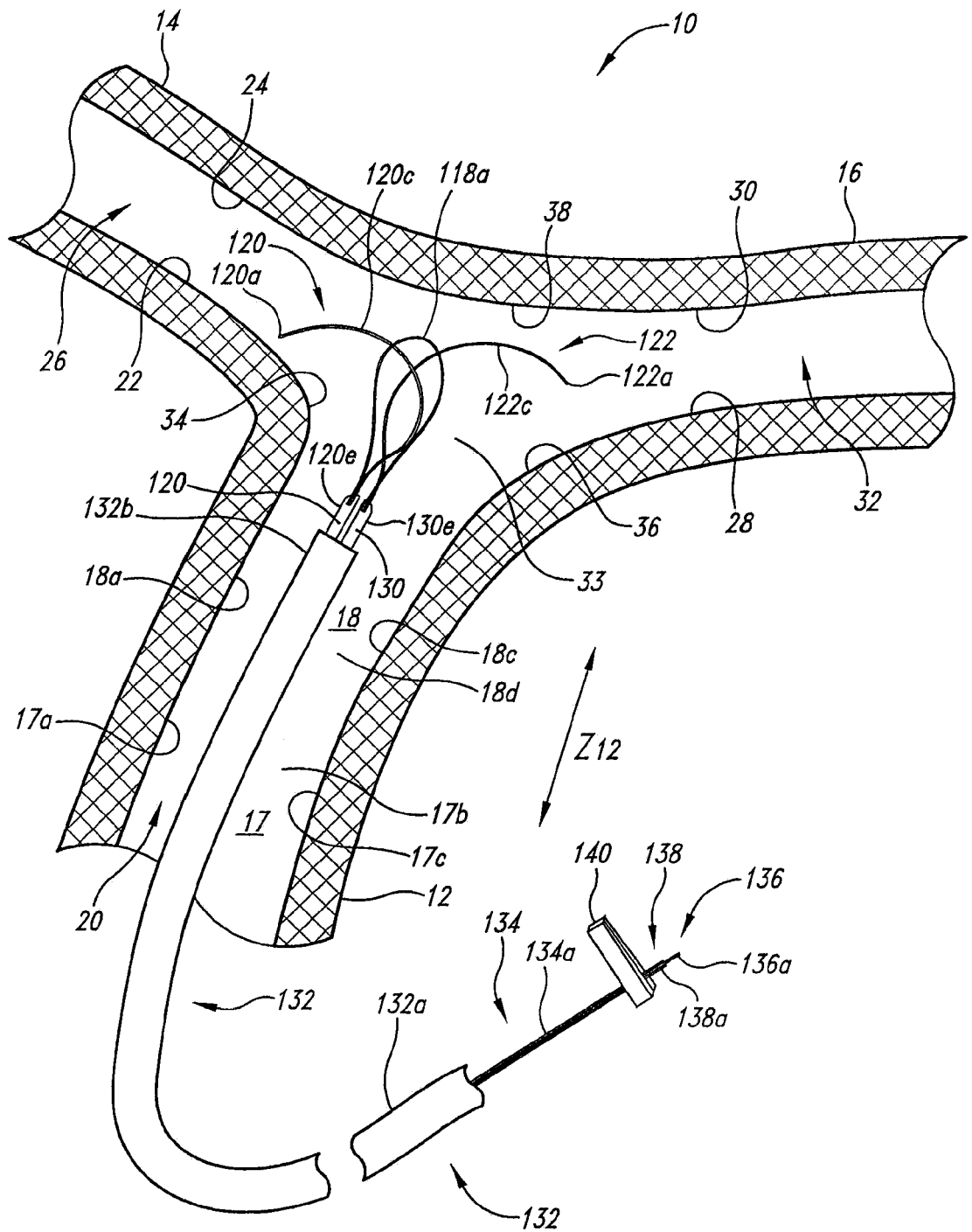

FIG. 31 is a sectional fragmented view of the bifurcated vasculature of FIG. 1 taken along the 1A-1A line and a front elevational fragmentary view of the second catheter end inserted into the vascular trunk with a portion of the third vascular anchoring system extending therefrom by a second amount and the first catheter end external to the bifurcated vasculature with the first end of the deployment tether extending therefrom by a second diminished amount.

Figure 32:
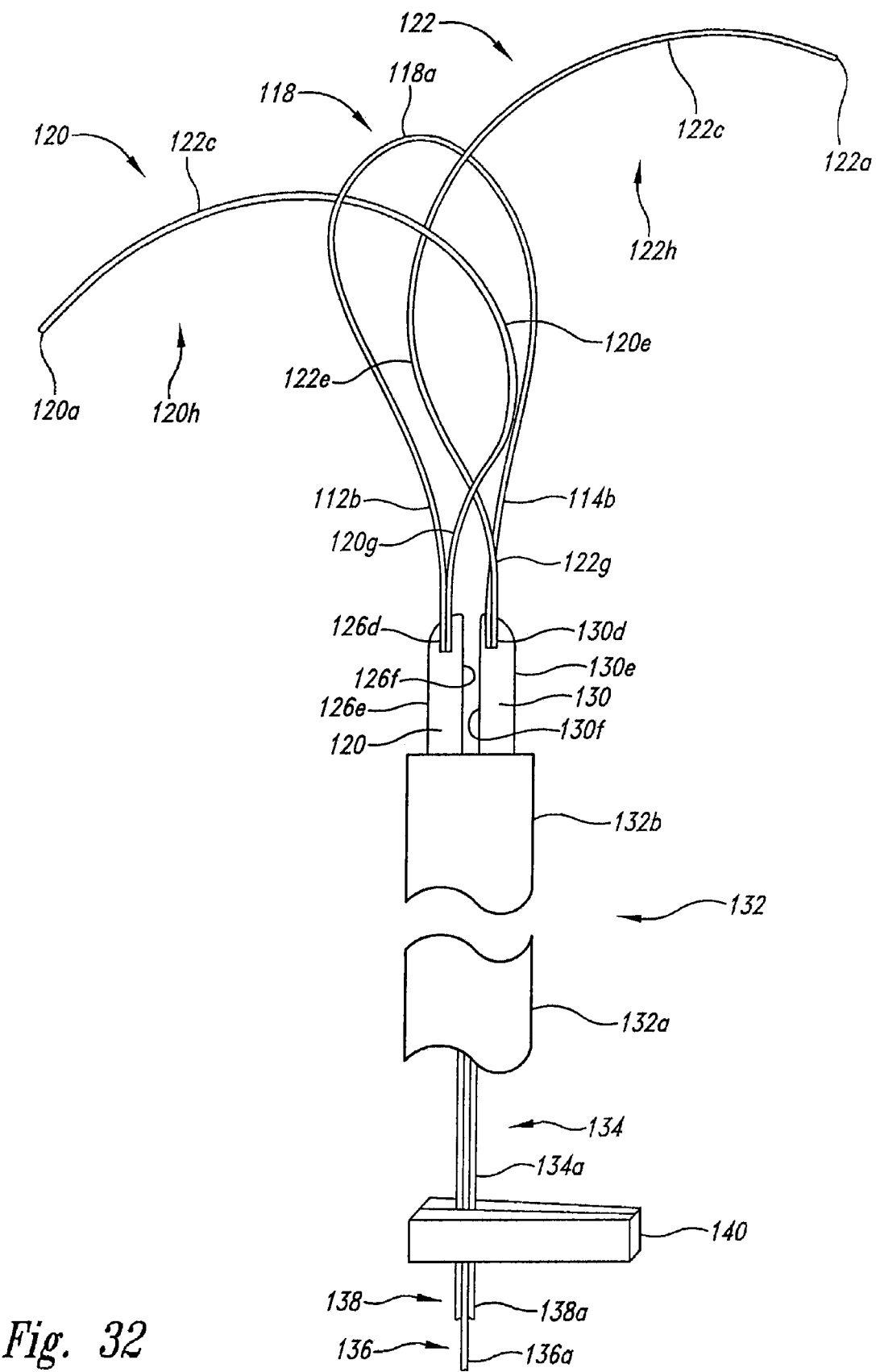

FIG. 32 is an enlarged view of the front elevational fragmentary view of the second catheter end with the portion of the third vascular anchoring system extending therefrom by the second amount and the first catheter end with the first end of the deployment tether extending therefrom by the second diminished amount of FIG. 31.

Figure 33:
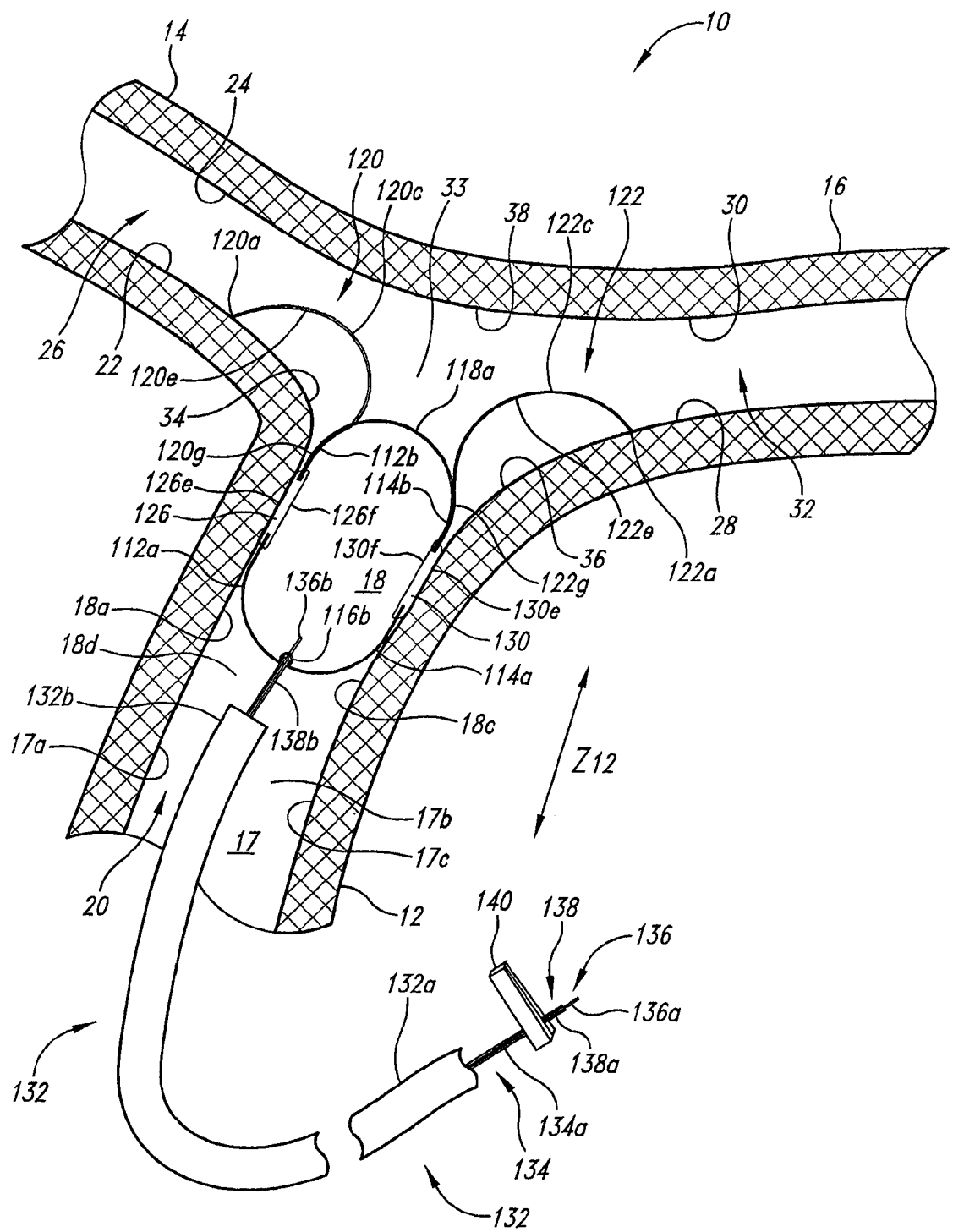

FIG. 33 is a sectional fragmented view of the bifurcated vasculature of FIG. 1 taken along the 1A-1A line and a front elevational fragmentary view of the second catheter end inserted into the vascular trunk with the third vascular anchoring system extending therefrom by a fully extended amount and coupled with the second end of the deployment tether extending therefrom by a first extended amount and the first catheter end external to the bifurcated vasculature with the first end of the deployment tether extending therefrom by a third diminished amount.

Figure 34:
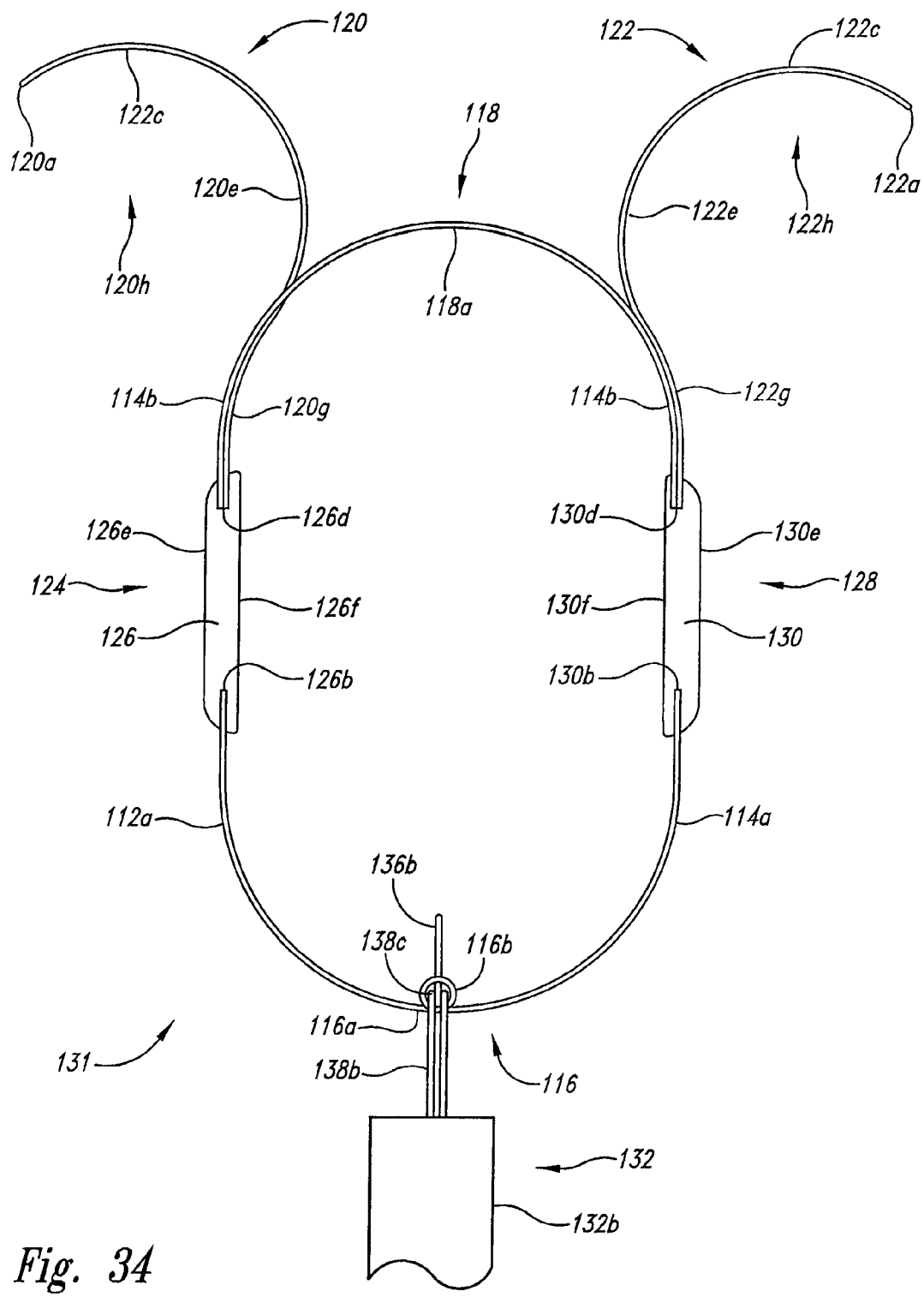

FIG. 34 is an enlarged view of the front elevational fragmentary view of the second catheter end of FIG. 31 with the third vascular anchoring system fully extended therefrom shown coupled with the second end of the deployment tether extending therefrom.

Figure 35:
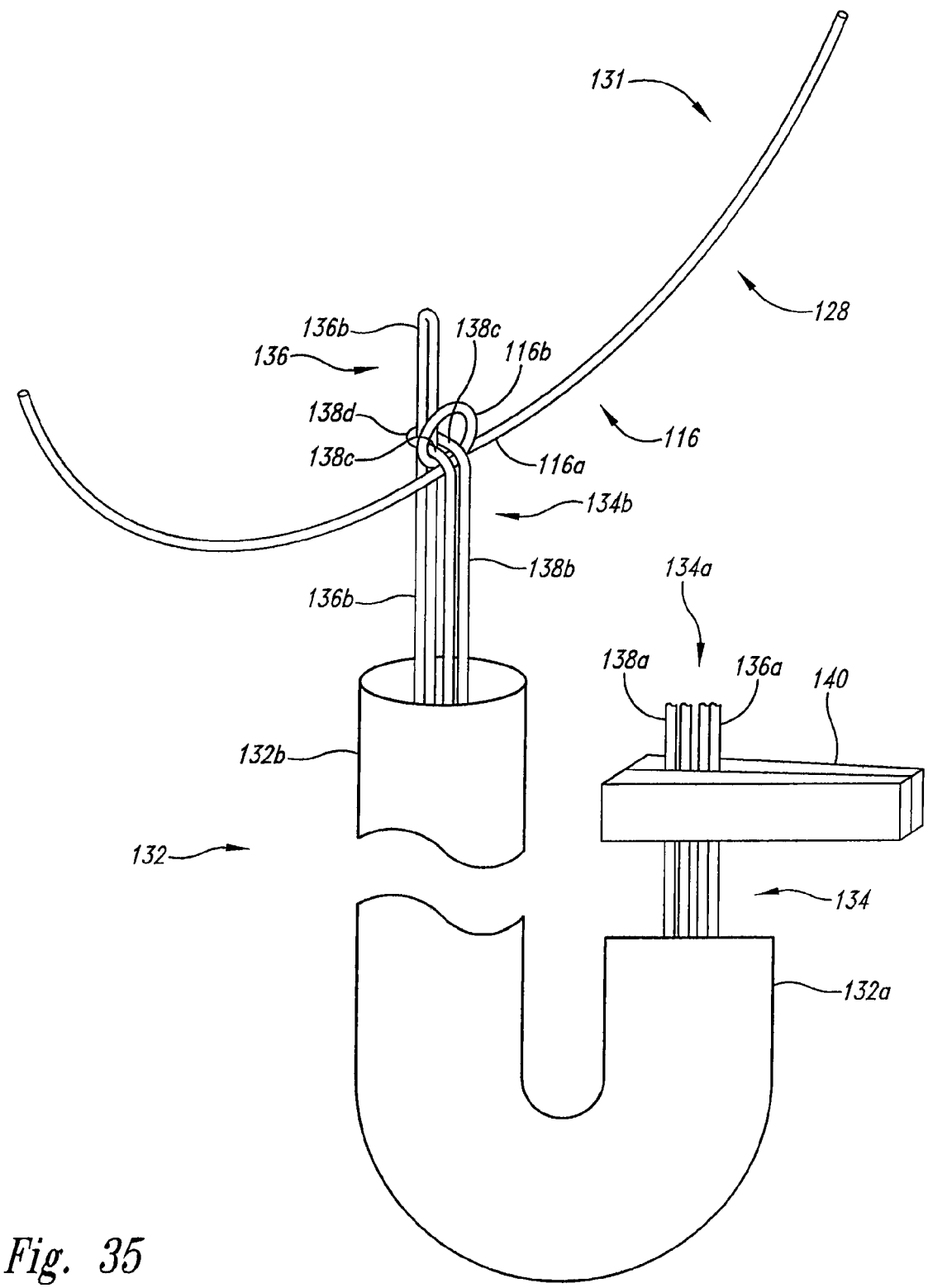

FIG. 35 is an enlarged fragmentary view of the third vascular anchoring system fully extended from the catheter and coupled with the second end of the deployment tether extended from the second catheter end and an enlarged fragmentary view of the first catheter end with the first end of the deployment tether extended therefrom.

Figure 36:
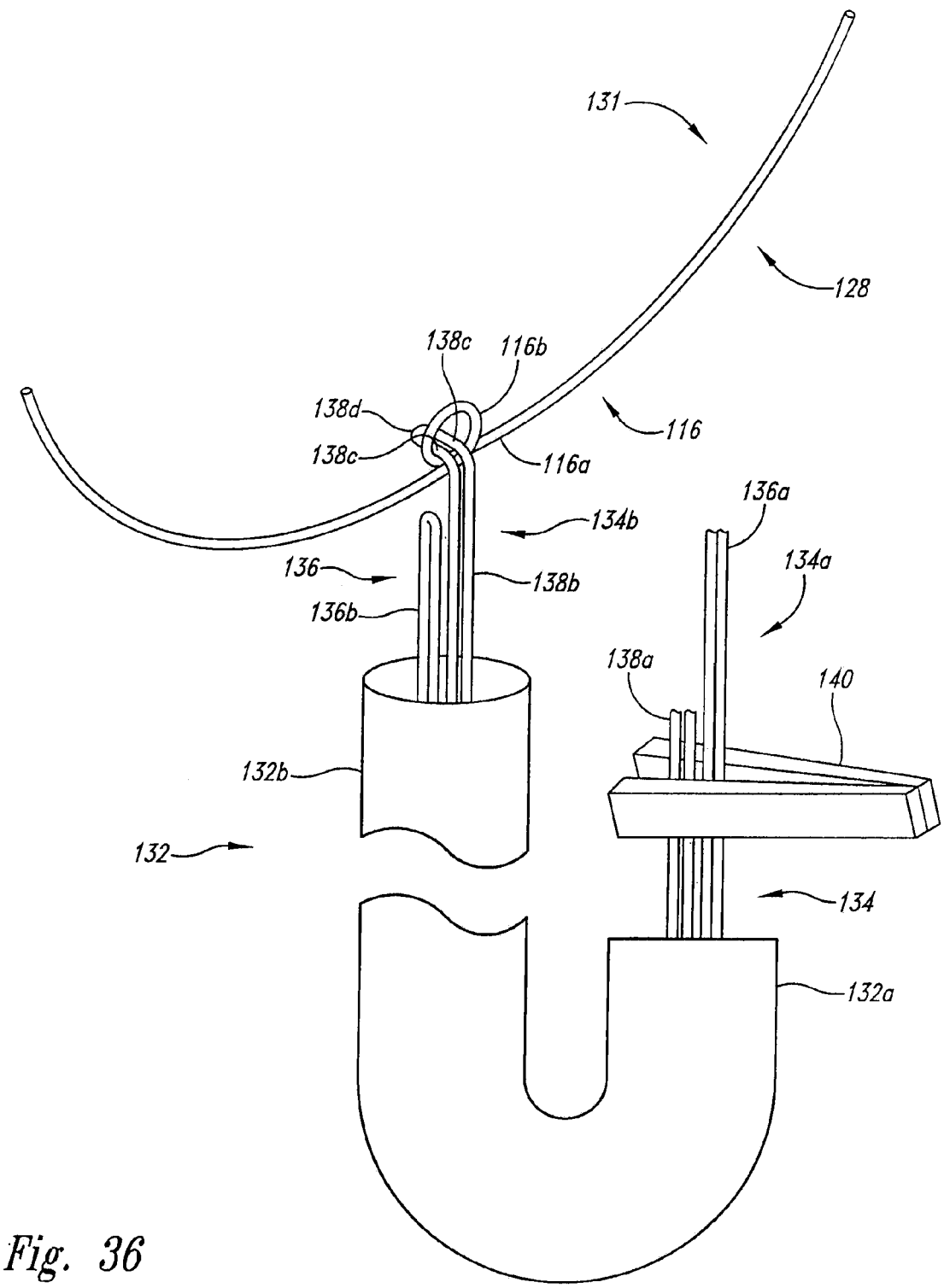

FIG. 36 is an enlarged fragmentary view of the third vascular anchoring system fully extended from the catheter and partially coupled with the second end of the deployment tether extended from the second catheter end with the deployment tether lock pin member uncoupled from the deployment tether hook member and an enlarged fragmentary view of the first catheter end with the first end of the deployment tether extended therefrom.

Figure 37:
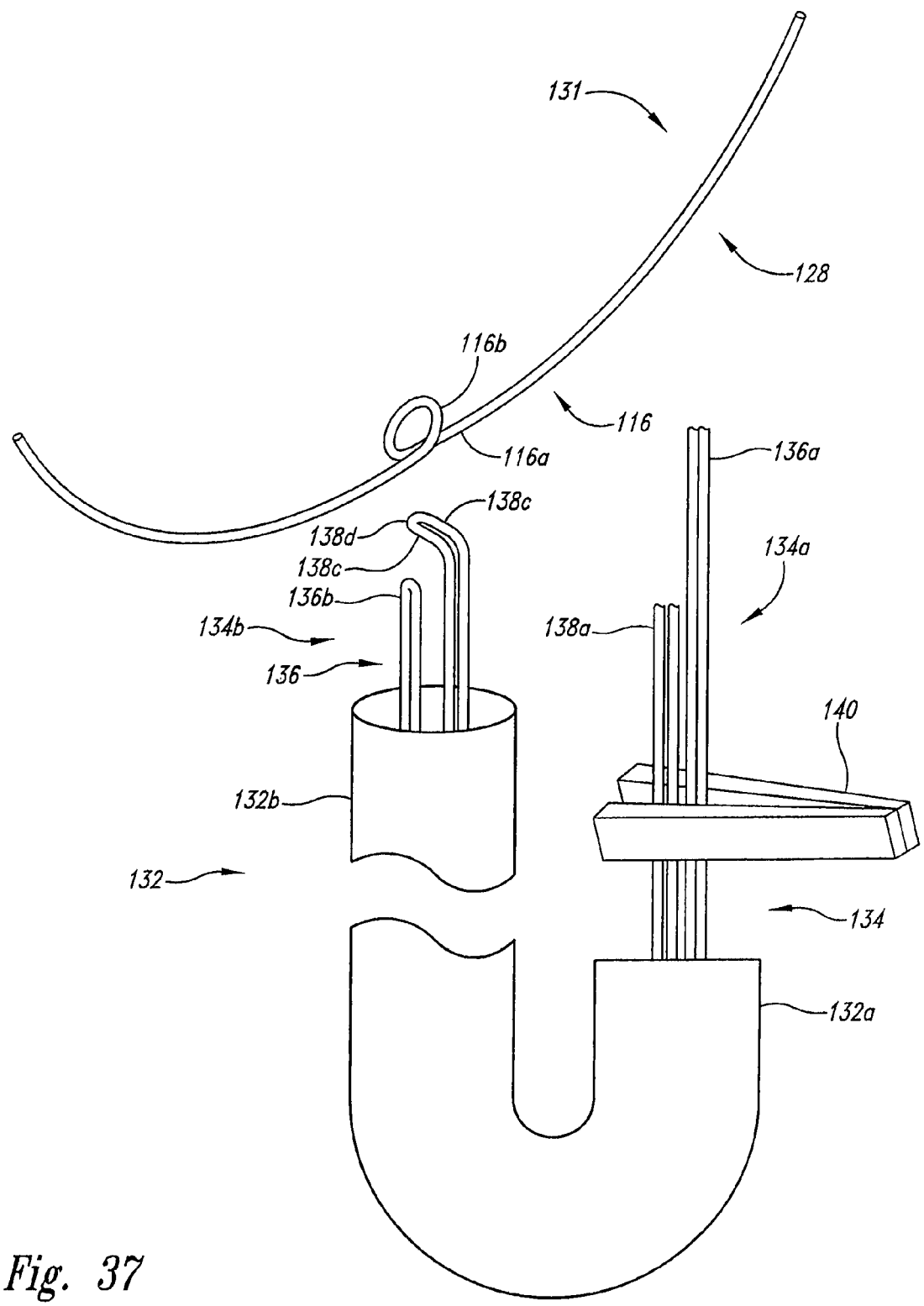

FIG. 37 is an enlarged fragmentary view of the third vascular anchoring system fully extended from the catheter and uncoupled from the second end of the deployment tether, which is extended from the second catheter end and an enlarged fragmentary view of the first catheter end with the first end of the deployment tether extended therefrom.

Figure 38:
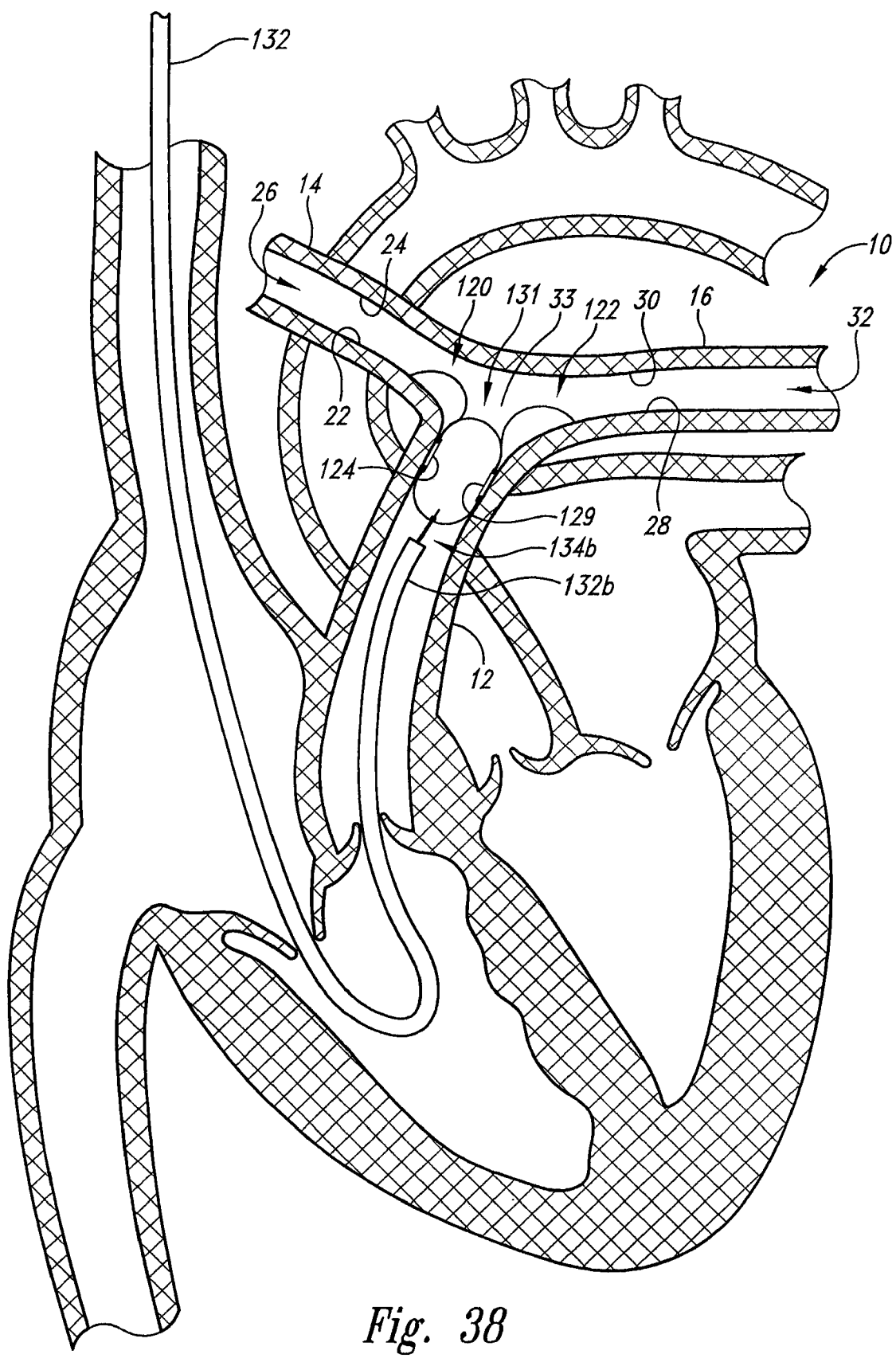

FIG. 38 is a sectional view of an exemplary heart region as the vascular area with a front elevational view of the third vascular anchoring system fully extended from the catheter into a pulmonary artery, engaging with the associated left and right pulmonary arteries and shown coupled with the deployment tether before being fully deployed.

Figure 39:
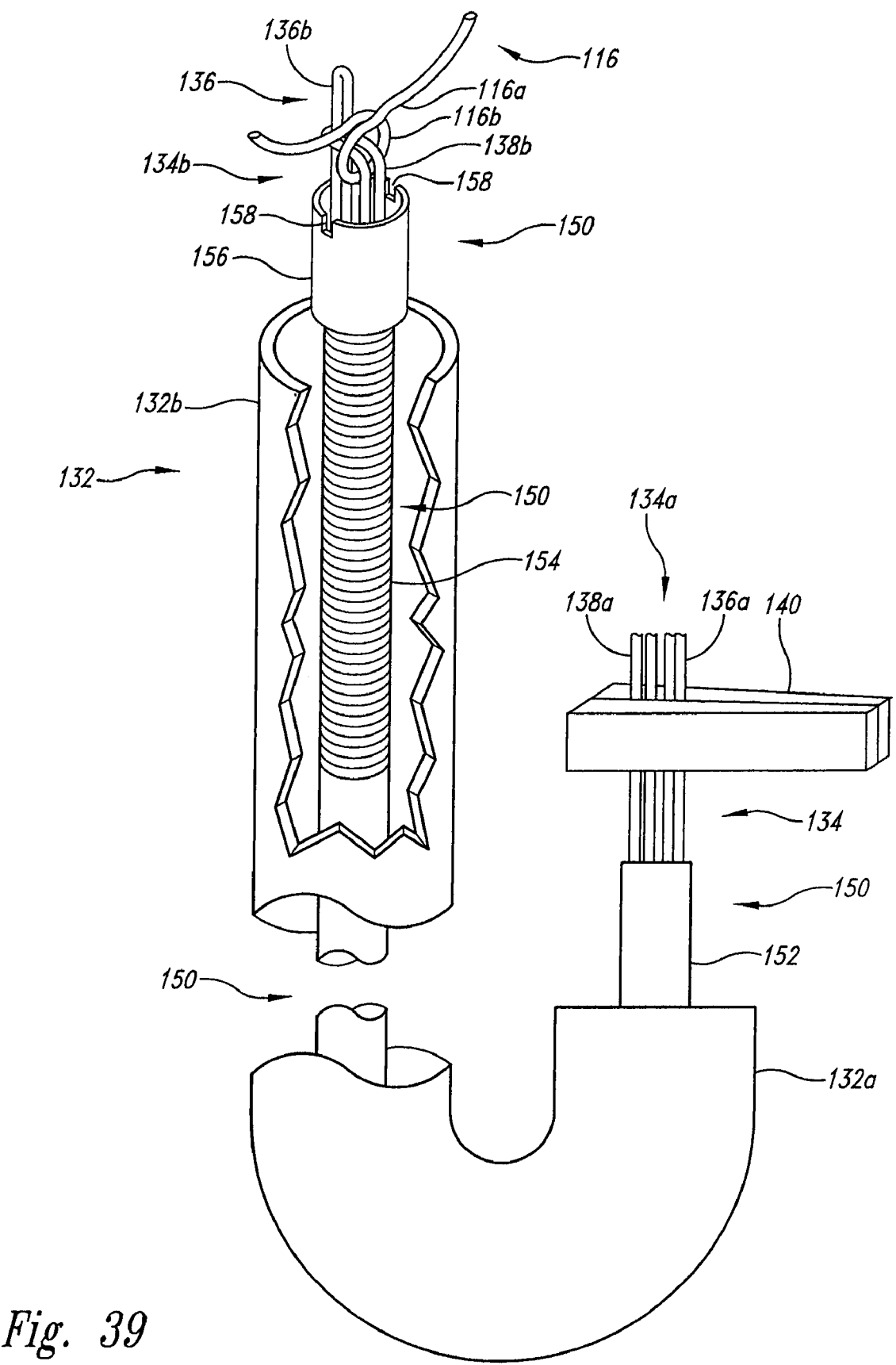

FIG. 39 is a sectional perspective view of a first alternative implementation of the deployment tether to include an alignment conduit.

Figure 40:
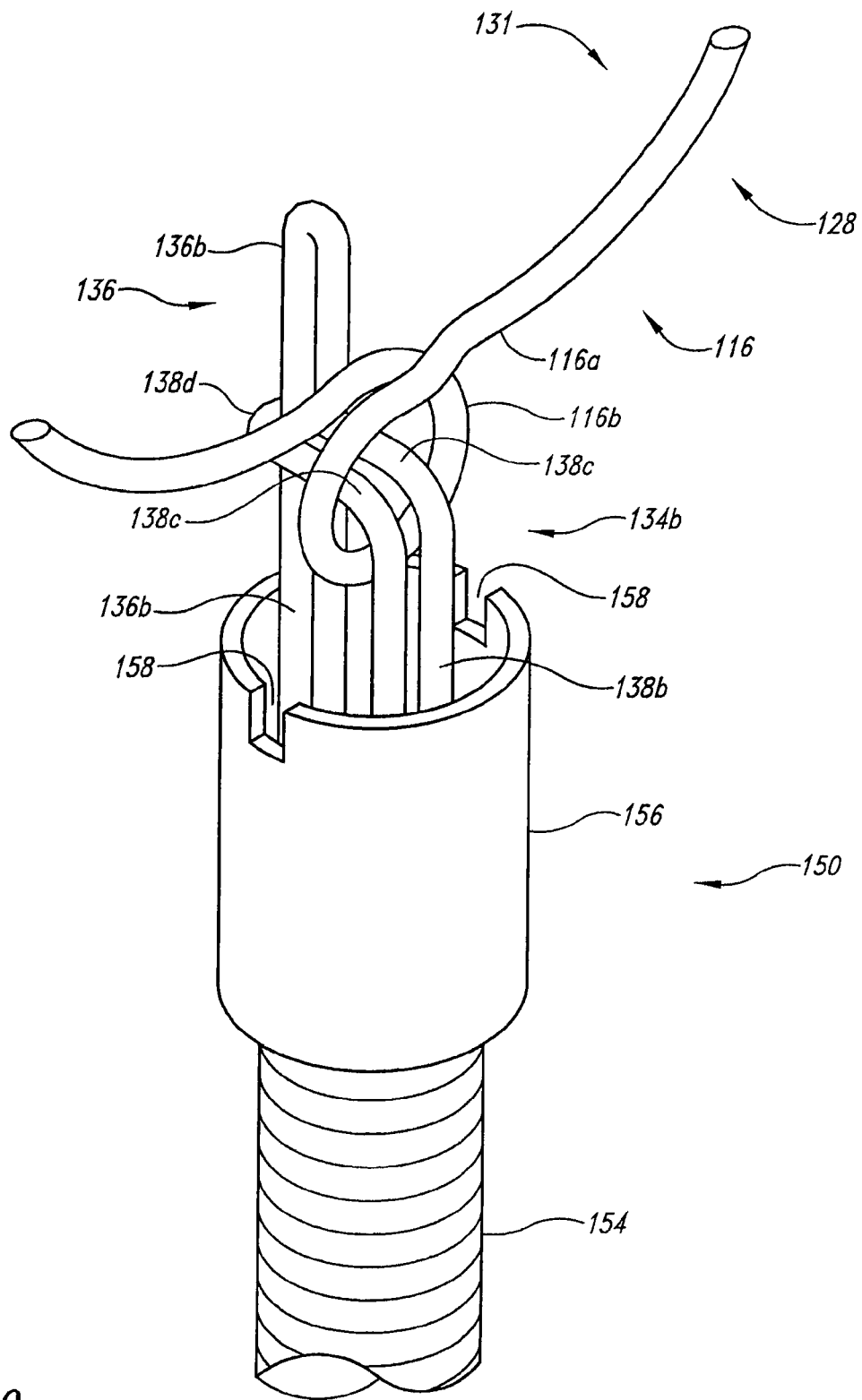

FIG. 40 is an enlarged fragmentary perspective view of the alignment conduit of FIG. 39 before engagement of the vascular anchoring system.

Figure 41:
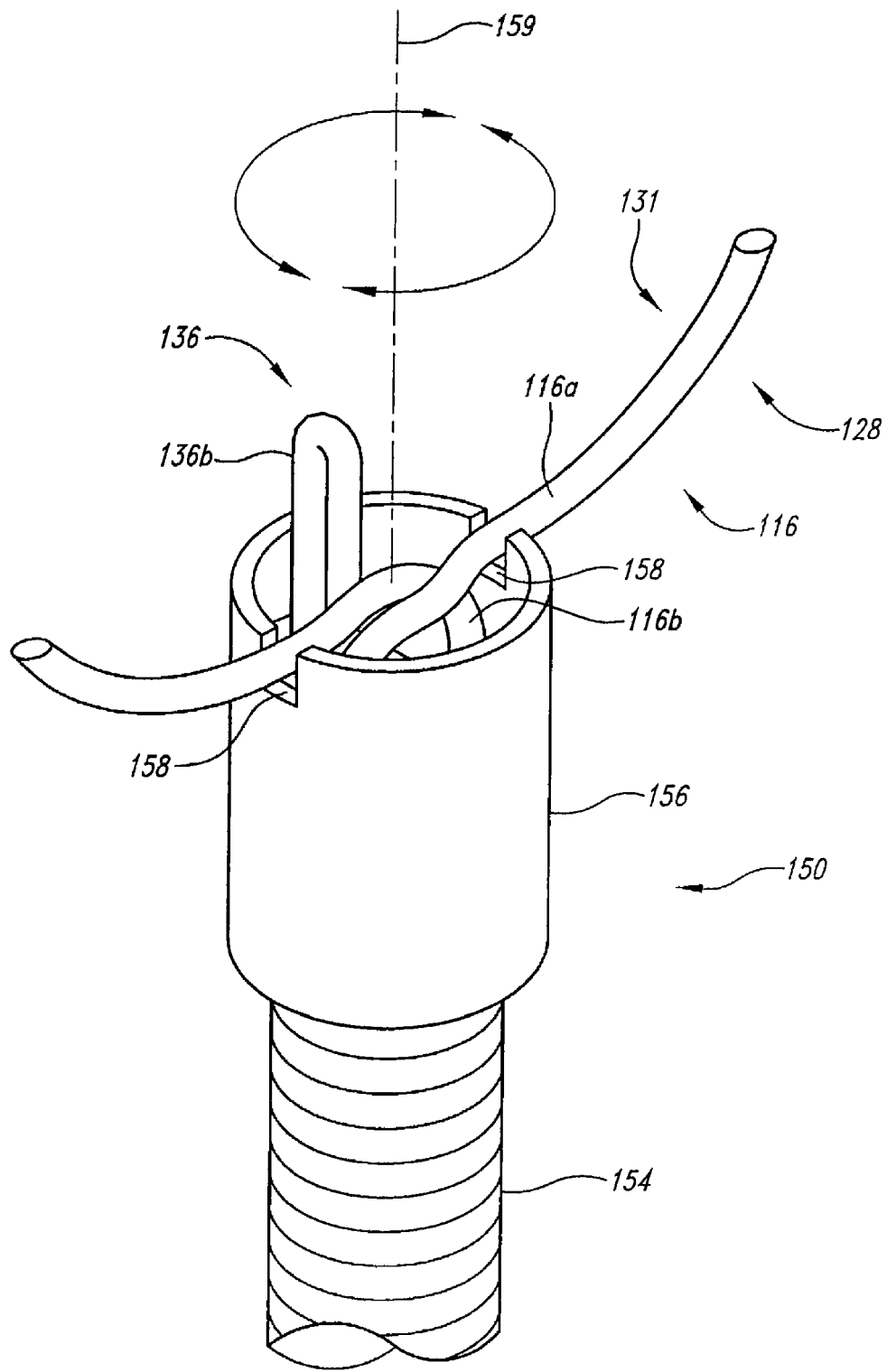

FIG. 41 is an enlarged fragmentary perspective view of the alignment conduit of FIG. 39 as engaged with the vascular anchoring system.

Figure 42:
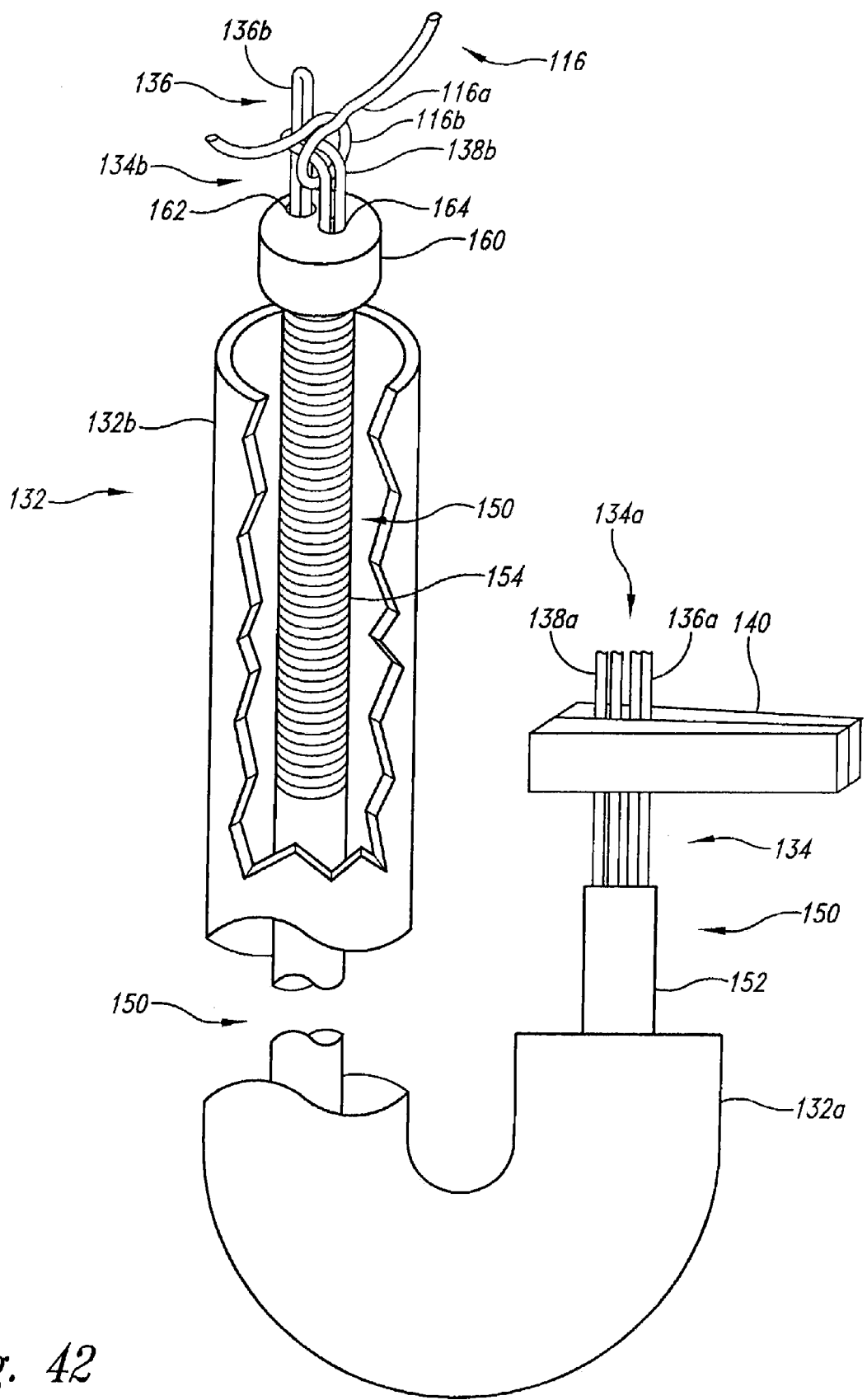

FIG. 42 is a sectional perspective view of an alternative engagement portion of the alignment conduit of FIG. 39.

Figure 43:
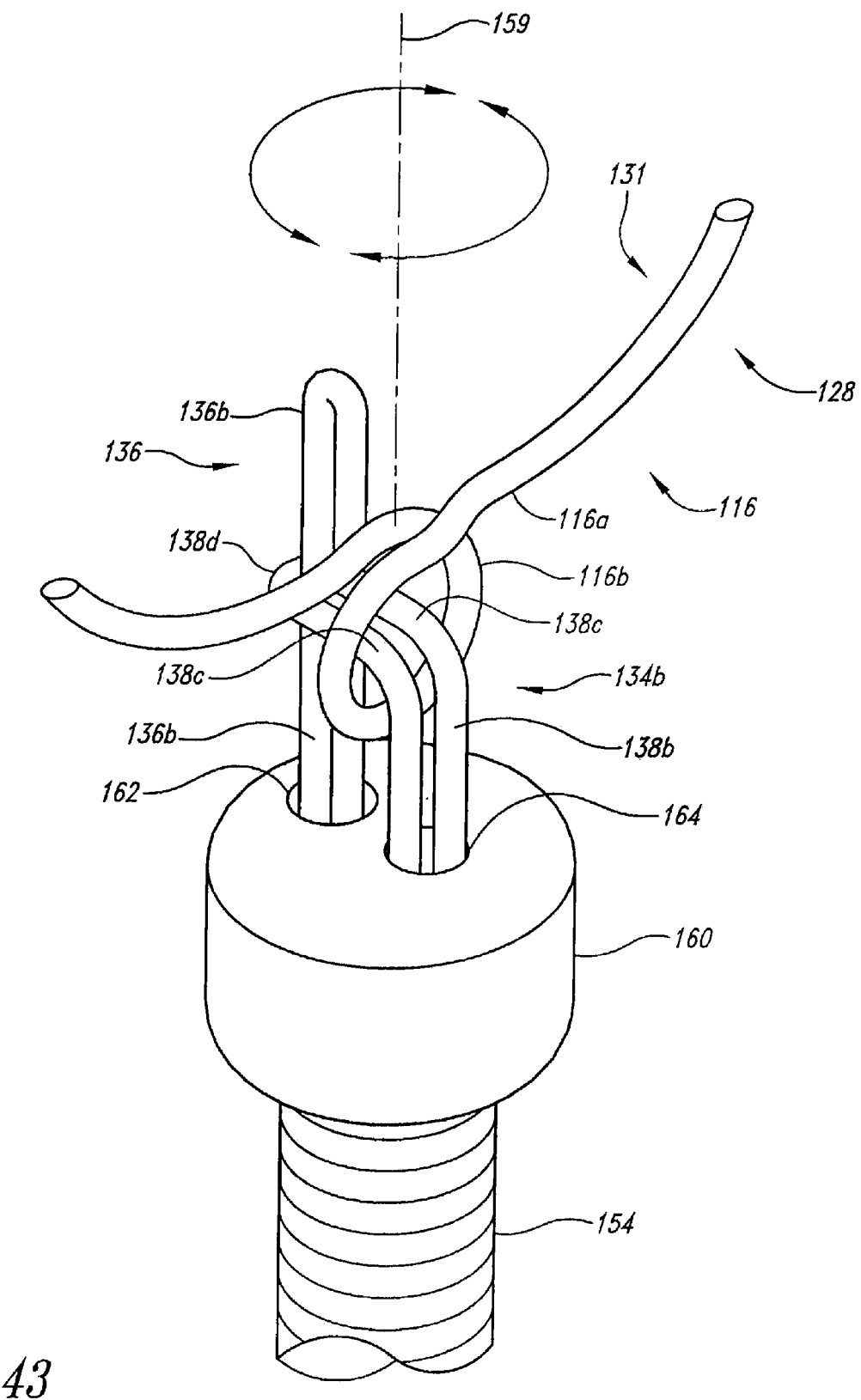

FIG. 43 is an enlarged fragmentary perspective view of the alternative engagement portion of FIG. 42.

DETAILED DESCRIPTION OF THE INVENTION

As described herein vascular anchoring systems are used to position an implant in a vascular area such as a bifurcated vasculature with relatively high fluid flow, for instance, in an area of a pulmonary artery with associated left and right pulmonary arteries.

Figure 1A:
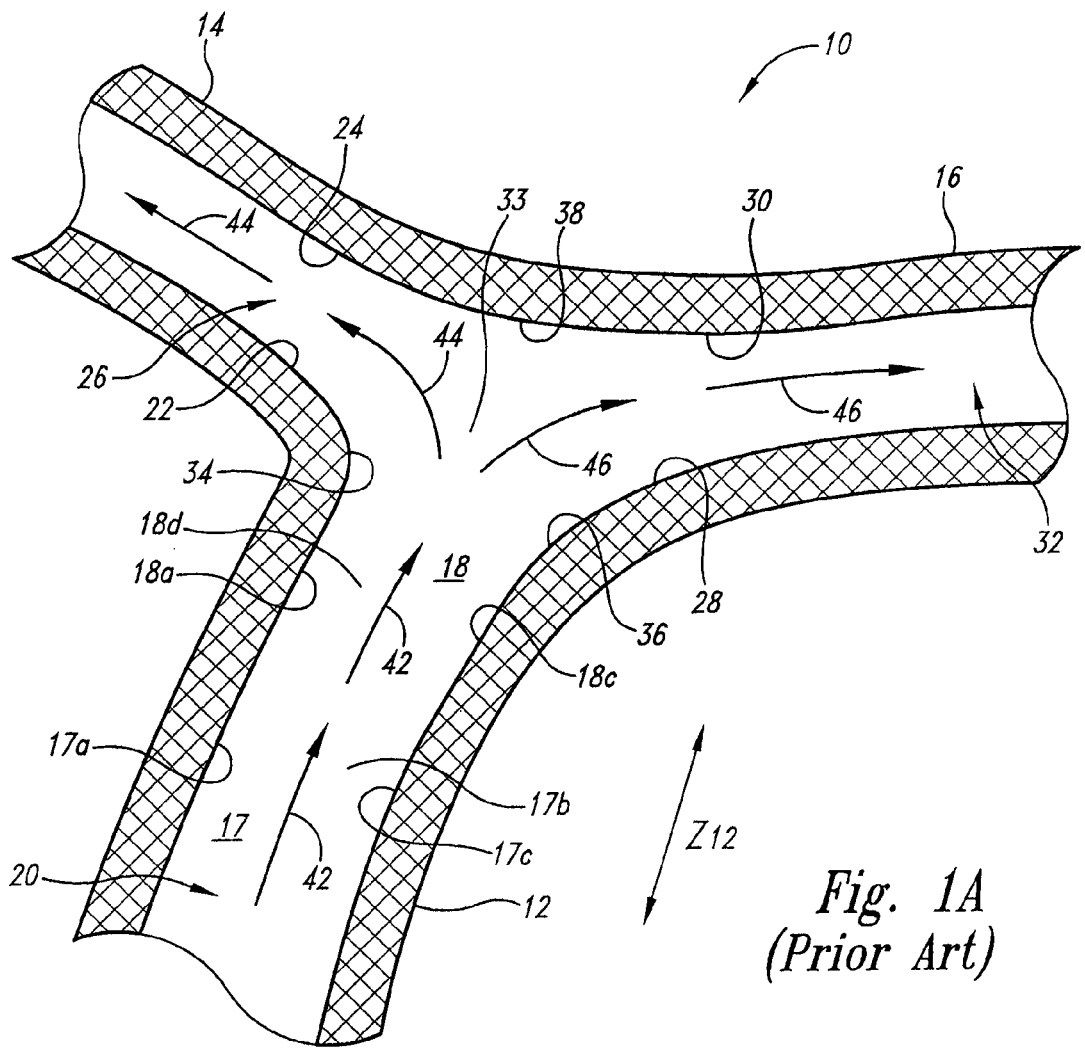
FIG. 1A is a sectional fragmented view of the bifurcated vasculature of FIG. 1 taken along the 1A-1A line with fluid flow proceeding from a vascular trunk to a pair of first and second vascular branches.
Figure 1B:
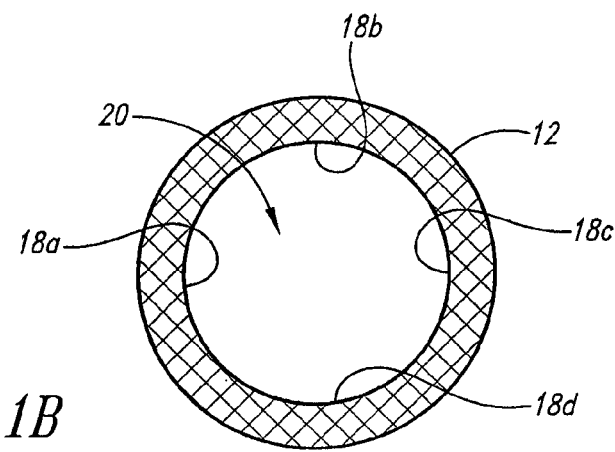
FIG. 1B is a sectional view of the vascular trunk of the bifurcated vasculature of FIG. 1 taken along the 1B-1B line.

As shown in FIG. 1 an exemplary vascular area is depicted as a bifurcated vasculature 10 to receive versions of the vascular anchoring system disclosed herein. The bifurcated vasculature 10 is shown in FIG. 1A has having a vascular trunk 12 that extends longitudinally approximately along a dimensional axis Z and splits into a first vascular branch 14 and a second vascular branch 16. For illustrative purposes the vascular trunk 12 has been depicted in the Figures including FIGS. 1A and 1B with labels as having four distal surface locations of a distal trunk surface portion 17: a first distal surface location 17a, a second distal surface location 17b, a third distal surface location 17c, and a fourth distal surface location 17d and as having four proximate surface locations of a proximate trunk surface portion 18: a first proximate surface location 18a, a second proximate surface location 18b, a third proximate surface location 18c, and a fourth proximate surface location 18d, which will be used herein to describe placement of portions of the vascular anchoring systems.

The distal trunk surface portion 17 is farther along the dimensional Z-axis from the first vascular branch and the second vascular branch than the proximate trunk surface portion 18. Those surface locations labeled sharing like ending letters, such as the first distal surface location 17a and the first proximate surface location 18a, are substantially spaced from one another substantially along the longitudinal direction of the dimensional axis Z.

The first distal surface location 17a is positioned substantially directly across from the third distal surface location 17c, which have substantially the same longitudinal position along the dimensional Z axis. The second distal surface location 17b is positioned substantially directly across from the fourth distal surface location 17d, which have substantially the same longitudinal position along the dimensional Z-axis. The positions of the second distal surface location 17b and the fourth distal surface location 17d are farther from the first vascular branch 14 and the second vascular branch 16 along the dimensional Z axis than the positions of the first distal surface location 17a and the third distal surface location 17c are to the first vascular branch 14 and the second vascular branch 16.

The first proximate surface location 18a is positioned substantially directly across from the third proximate surface location 18c, which have substantially the same longitudinal position along the dimensional Z-axis. The second proximate surface location 18b is positioned substantially directly across from the fourth proximate surface location 18d, which have substantially the same longitudinal position along the dimensional Z-axis. The positions of the second proximate surface location 18b and the fourth proximate surface location 18d are closer to the first vascular branch 14 and the second vascular branch 16 along the dimensional Z axis than the positions of the first proximate surface location 18a and the third proximate surface location 18c are to the first vascular branch 14 and the second vascular branch 16.

The first vascular branch 14 is shown in FIG. 1A to have a first branch proximate surface 22, a first branch distal surface 24, and a first branch interior 26. The first branch proximate surface 22 is relatively closer along the dimensional axis Z to the vascular trunk 12 than the first branch distal surface 24. The second vascular branch 16 has a second branch proximate surface 28, a second branch distal surface 30, and a second branch interior 32. The second branch proximate surface 28 is relatively closer along the dimensional axis Z to the vascular trunk 12 than the second branch distal surface 30.

The vascular trunk 12, the first vascular branch 14, and the second vascular branch 16 join at a vascular intersection 33. The vascular intersection 33 has a first proximate intersection surface 34, a second proximate intersection surface 36, and a distal intersection surface 38. Between the vascular trunk 12 and the first vascular branch 14 lays the first proximate intersection surface 34. Between the vascular trunk 12 and the second vascular branch 16 lays the second proximate intersection surface 36. Farther from the vascular trunk 12 along the longitudinal dimension Z lays the distal intersection surface 38.

Figure 2:
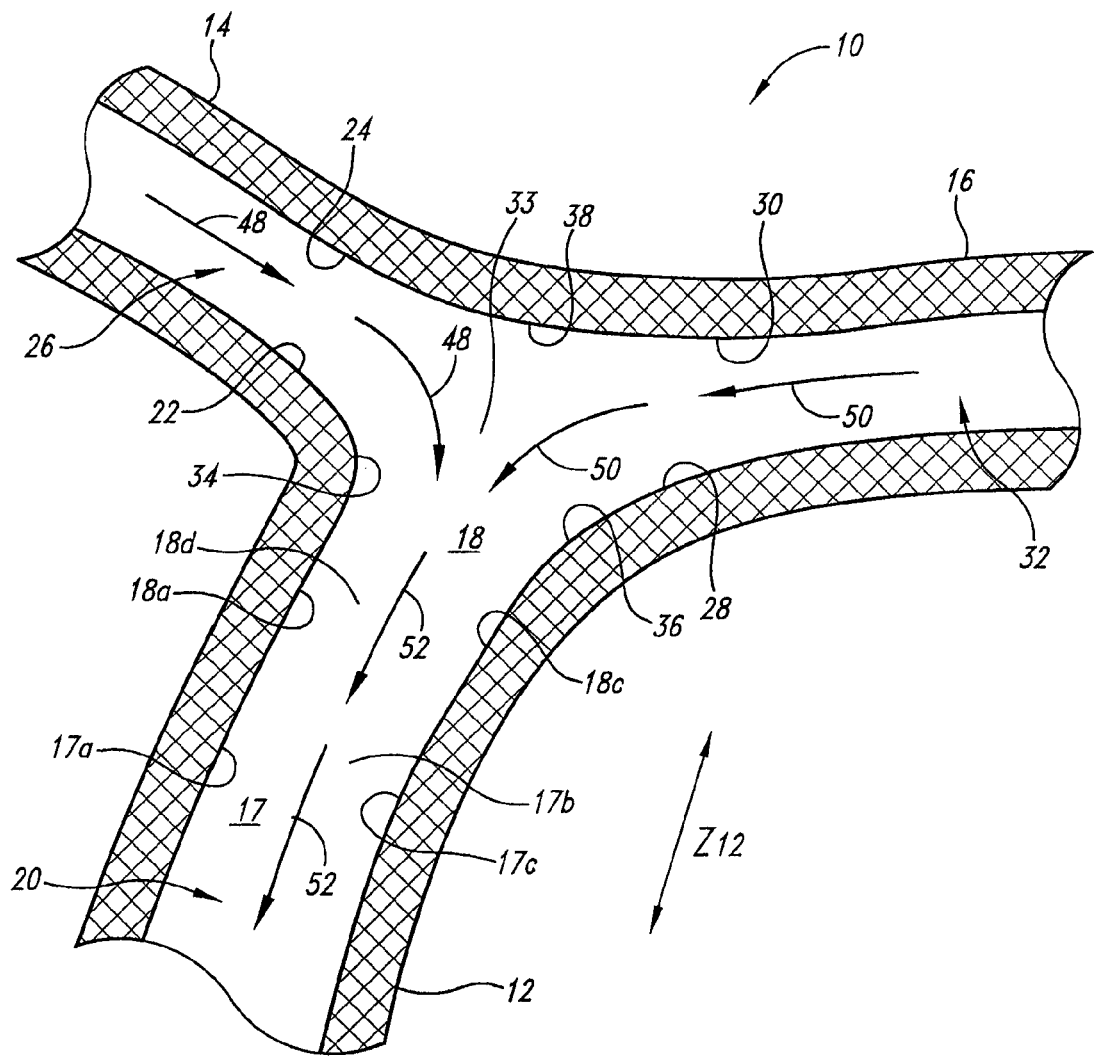
FIG. 2 is a sectional fragmented view of the bifurcated vasculature of FIG. 1 taken along the 2-2 line with fluid flow proceeding from the first and second vascular branches to the vascular trunk.

The intersection surfaces serve to bound an intersection 33 that is positioned between the vascular trunk 12 and the first vascular branch 14, and the second vascular branch 16. The bifurcated vasculature 10 is shown in FIG. 1A as generally having fluid flow from the vascular trunk 12 to the first vascular branch 14 and the second vascular branch 16 with vascular trunk divergent fluid flow 42, first vascular branch divergent fluid flow 44, and second vascular branch divergent fluid flow 46. The bifurcated vasculature 10 is shown in FIG. 2 as generally having fluid flow from the first vascular branch 14 and the second vascular branch 16 to the vascular trunk 12 with first vascular branch convergent fluid flow 48, second vascular branch convergent fluid flow 50, and vascular trunk convergent fluid flow 52.

Figure 3:
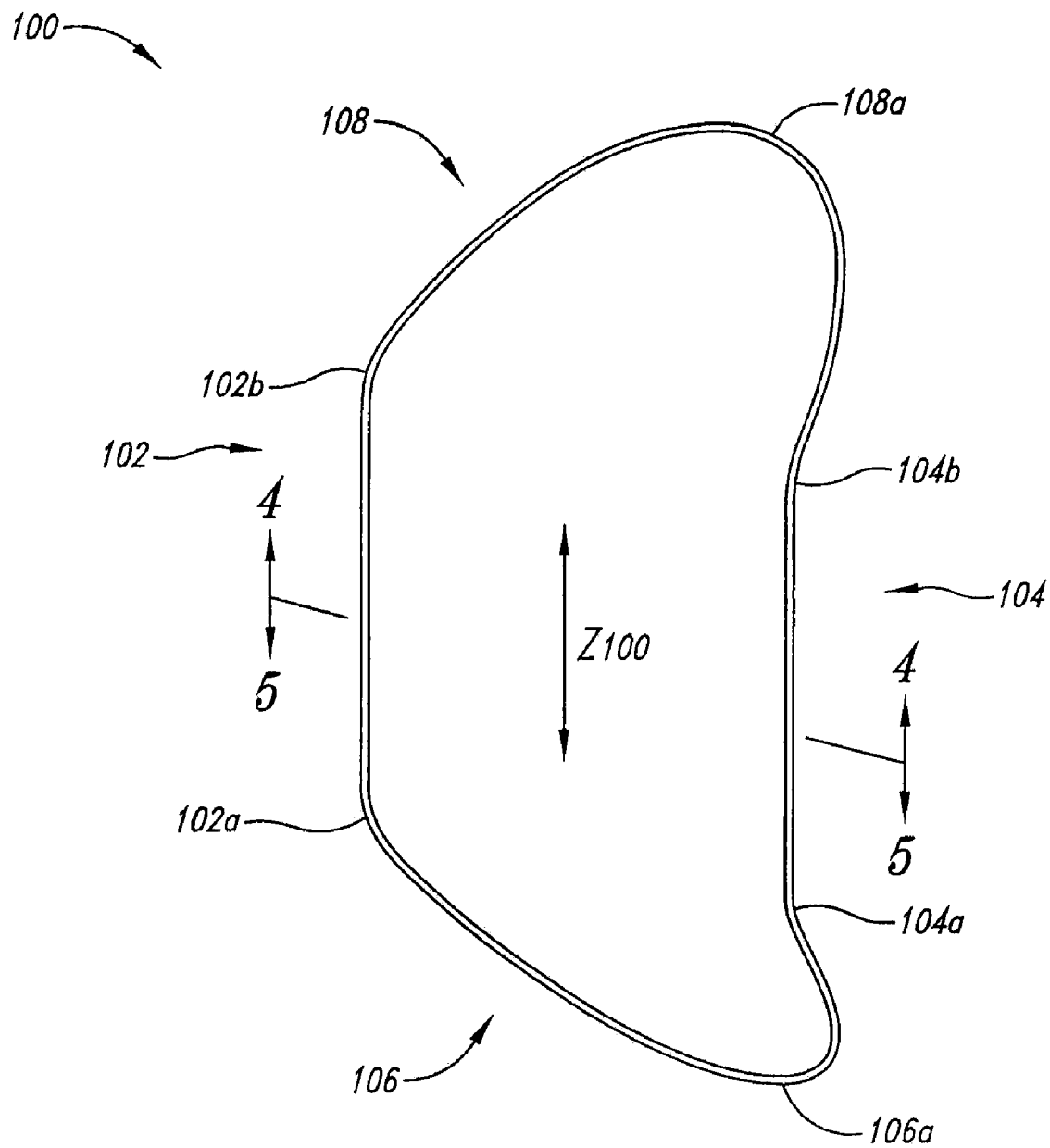
FIG. 3 is a perspective view of an exemplary first of a pair of two anchoring trunk sections of a first anchoring trunk member of the vascular anchoring system.

A first anchoring trunk section 100 is shown in FIG. 3 as having a first longitudinal member 102 with a first end 102a and a second end 102b and a second longitudinal member 104 spaced apart in juxtaposition therefrom with a first end 104a and a second end 104b. As shown in FIG. 3, both the first longitudinal member 102 and the second longitudinal member 104 extend substantially in the direction of the dimensional axis Z100. Extending between the first end 102a of the first longitudinal member 102 and the first end 104a of the second longitudinal member 104 is a first convex arch 106 with a first apex 106a. It is an object of this invention that the anchoring trunk section 100 be constructed so that it is flexible and compliant to the vessel wall, so that it neither damages the vessel wall nor restricts natural vessel wall motion. The shape of the trunk section 100 shown in FIG. 3 is chosen to provide these features.

The first apex 106a is positioned along the dimensional axis Z100 farther away from the second end 102b of the first longitudinal member 102 and the second end 104b of the second longitudinal member 104 than the first end 102a of the first longitudinal member is from the second end 102b and than the first end 104a of the second longitudinal member is from the second end 104b. Extending between the second end 102b of the first longitudinal member 102 and the second end 104b of the second longitudinal member 104 is a second convex arch 108 with a second apex 108a. The second apex 108a is positioned along the dimensional axis Z100 farther away from the first end 102a of the first longitudinal member 102 and the first end 104a of the second longitudinal member 104 than the second end 102b of the first longitudinal member is from the first end 102a and than the second end 104b of the second longitudinal member is from the first end 104a.

Figure 4:
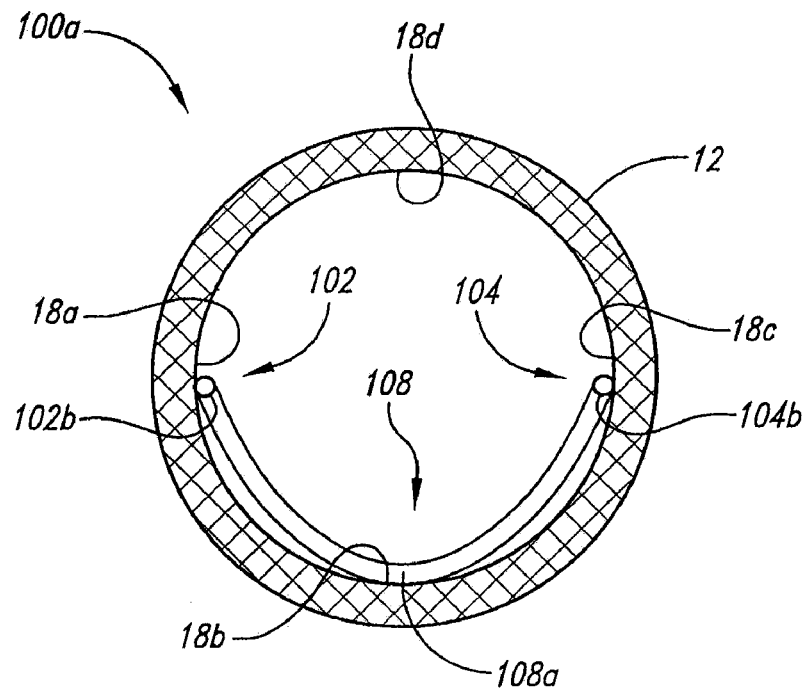
FIG. 4 is a sectional view of the first anchoring trunk section taken along the 4-4 line of FIG. 3 and a sectional view of the bifurcated vasculature taken along the 4-4 line of FIG. 1 with the first anchoring trunk section depicted as being inserted into the vascular trunk of the bifurcated vasculature.
Figure 5:
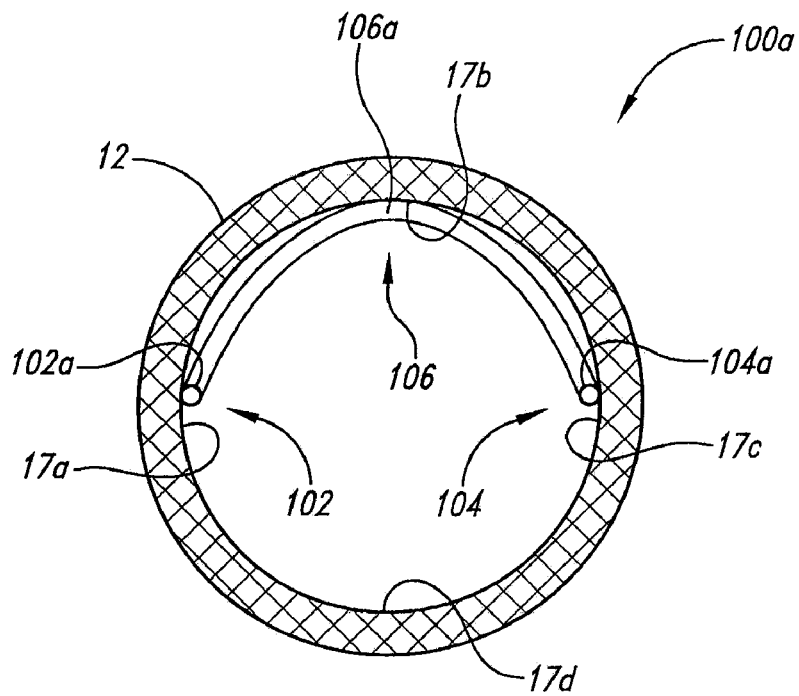
FIG. 5 is a sectional view of the first anchoring trunk section taken along the 5-5 line of FIG. 3 and a sectional view of the bifurcated vasculature taken along the 1B-1B line of FIG. 1 with the first anchoring trunk section depicted as being inserted into the vascular trunk of the bifurcated vasculature.

Although the first anchoring trunk section 100 may be used singly or in combination with other components, for illustrative purposes it is described herein in conjunction with other portions of vascular anchoring systems. FIGS. 4 and 5 depict what the first anchoring trunk section 100 would look like if it were placed alone inside of the vascular trunk 12 in a first position 100a. As shown in FIG. 4, the first longitudinal member 102 and the second longitudinal member 104 extend along the distal trunk surface portion 17 and the proximate trunk surface portion 18. The second convex arch 108 is shaped to substantially abut adjacent to the vascular trunk 12 extending substantially from the first proximate surface location 18a (where the second end 102b of the first longitudinal member 102 would be positioned) through the second proximate surface location 18b (where the second apex 108a would be positioned) on to the third proximate surface location 18c (where the second end 104b of the second longitudinal member 104 would be positioned).

As shown in FIG. 5, the first convex arch 106 is shaped to substantially abut adjacent to the vascular trunk 12 extending substantially from the first distal surface location 17a (where the first end 102a of the first longitudinal member 102 would be positioned) through the second distal surface location 17b (where the first apex 106a would be positioned) on to the third distal surface location 17c (where the first end 104a of the second longitudinal member 104 would be positioned).

Figure 6:
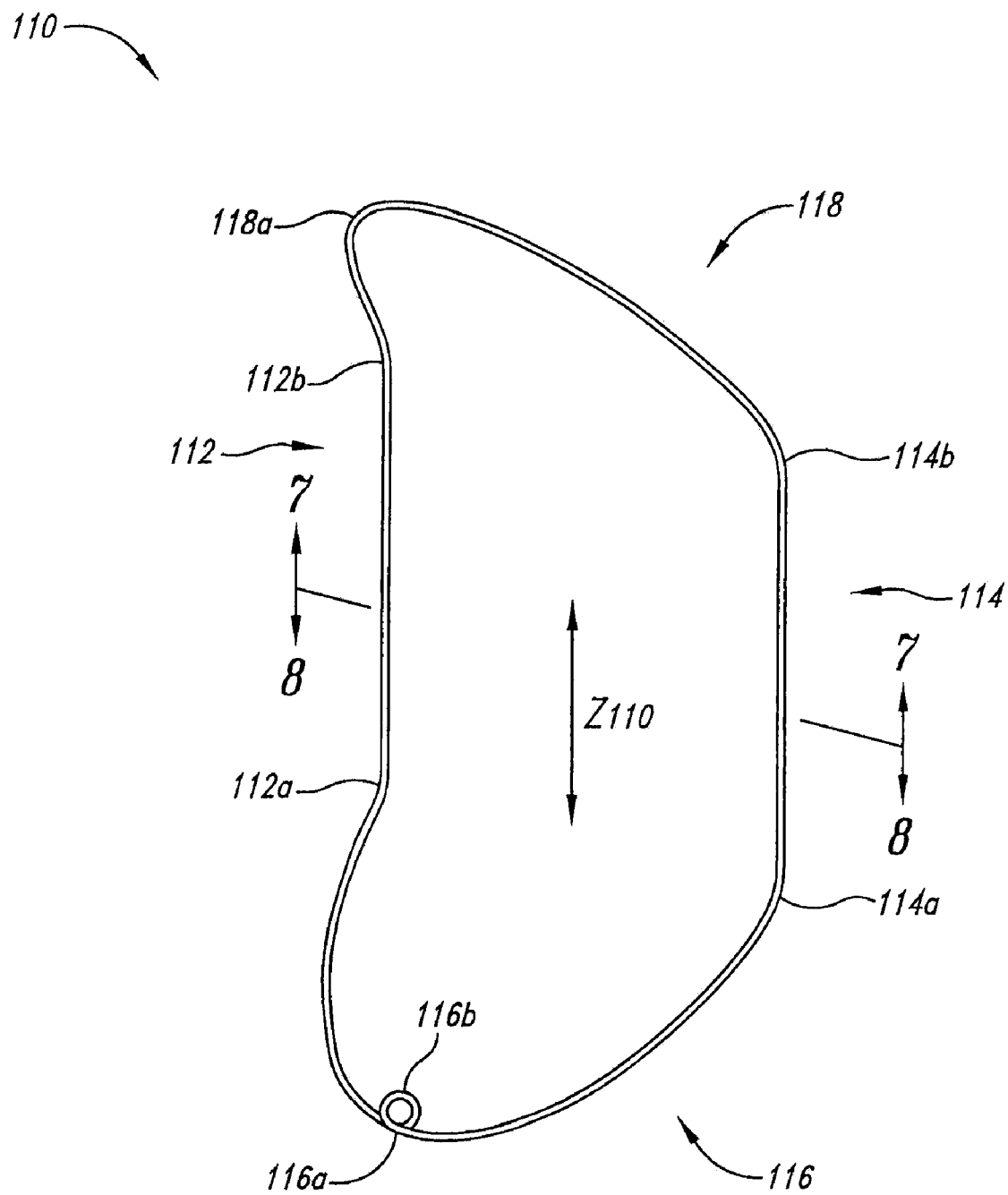
FIG. 6 is a perspective view of an exemplary second of the pair of the two anchoring sections of the first anchoring trunk member of the vascular anchoring system.

A second anchoring trunk section 110 is shown in FIG. 6 as having a first longitudinal member 112 with a first end 112a and a second end 112b and a second longitudinal member 114 spaced apart in juxtaposition therefrom with a first end 114a and a second end 114b. As shown in FIG. 6, both the first longitudinal member 112 and the second longitudinal member 114 extend substantially in the same direction as a dimensional axis Z110. Extending between the first end 112a of the first longitudinal member 112 and the first end 114a of the second longitudinal member 114 is a first convex arch 116 with a first apex 116a. The first apex 116a is positioned along the dimensional axis Z10 farther away from the second end 112b of the first longitudinal member 112 and the second end 114b of the second longitudinal member 114 than the first end 112a of the first longitudinal member is from the second end 112b and than the first end 114a of the second longitudinal member is from the second end 114b.

Extending between the second end 112b of the first longitudinal member 112 and the second end 114b of the second longitudinal member 114 is a second convex arch 118 with a second apex 118a. The second apex 118a is positioned along the dimensional axis Z110 farther away from the first end 112a from the first longitudinal member 112 and the first end 114a of the second longitudinal member 114 than the second end 112b of the first longitudinal member 112 is from the first end 112a and the second end 114b of the second longitudinal member 114 is from the first end 114a.

Figure 7:
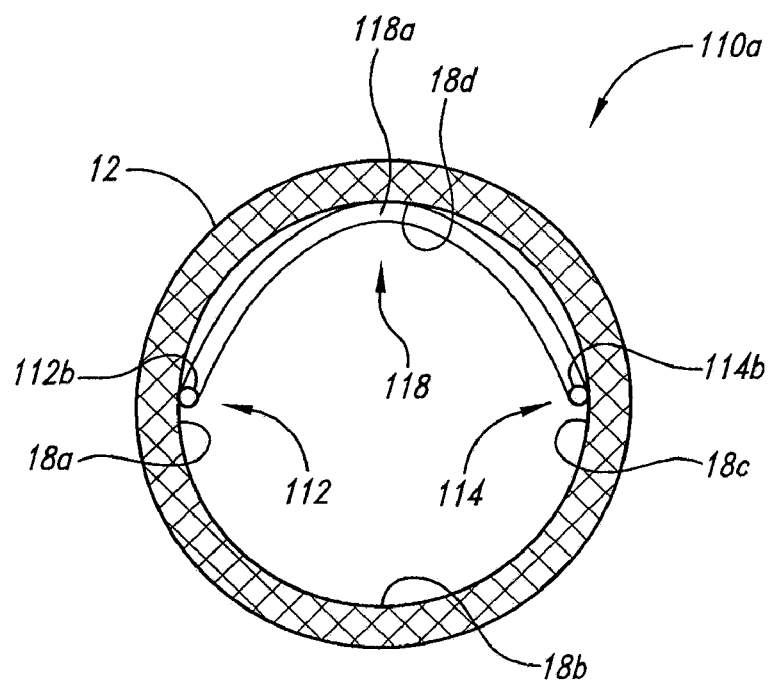
FIG. 7 is a sectional view of the second anchoring trunk section taken along the 7-7 line of FIG. 6 and a sectional view of the bifurcated vasculature taken along the 4-4 line of FIG. 1 with the second anchoring trunk section depicted as being inserted into the vascular trunk of the bifurcated vasculature.
Figure 8:
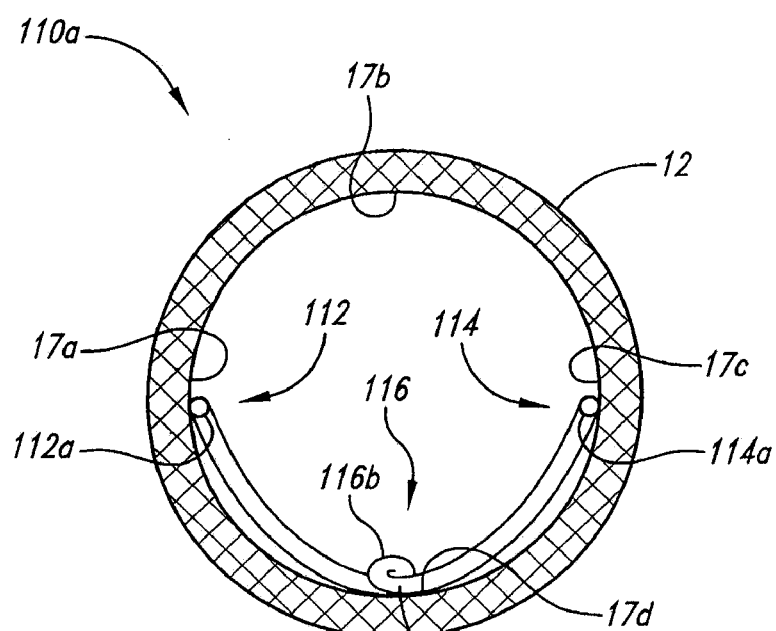
FIG. 8 is a sectional view of the second anchoring trunk section taken along the 8-8 line of FIG. 6 and a sectional view of the bifurcated vasculature taken along the 1B-1B line of FIG. 1 with the second anchoring trunk section depicted as being inserted into the vascular trunk of the bifurcated vasculature.

Although the second anchoring trunk section 110 may be used singly or in combination with other components, for illustrative purposes it is described herein in conjunction with other portions of vascular anchoring systems. FIGS. 7 and 8 depict what the second anchoring trunk section 110 would look like if it were placed alone inside of the vascular trunk 12 in a first position 110a. As shown in FIG. 7, the second convex arch 118 is shaped to substantially abut adjacent to the vascular trunk 12 extending substantially from the first proximate surface location 18a (where the second end 112b of the first longitudinal member 112 would be positioned) through the fourth proximate surface location 18d (where the second apex 118a would be positioned) on to the third proximate surface location 18c (where the second end 114b of the second longitudinal member 114 would be positioned).

As shown in FIG. 8, the first convex arch 116 is shaped to substantially abut adjacent to the vascular trunk 12 extending substantially from the first distal surface location 17a (where the first end 112a of the first longitudinal member 112 would be positioned) through the fourth distal surface location 17d (where the first apex 116a would be positioned) on to the third distal surface location 17c (where the first end 114a of the second longitudinal member 114 would be positioned).

Figure 9:
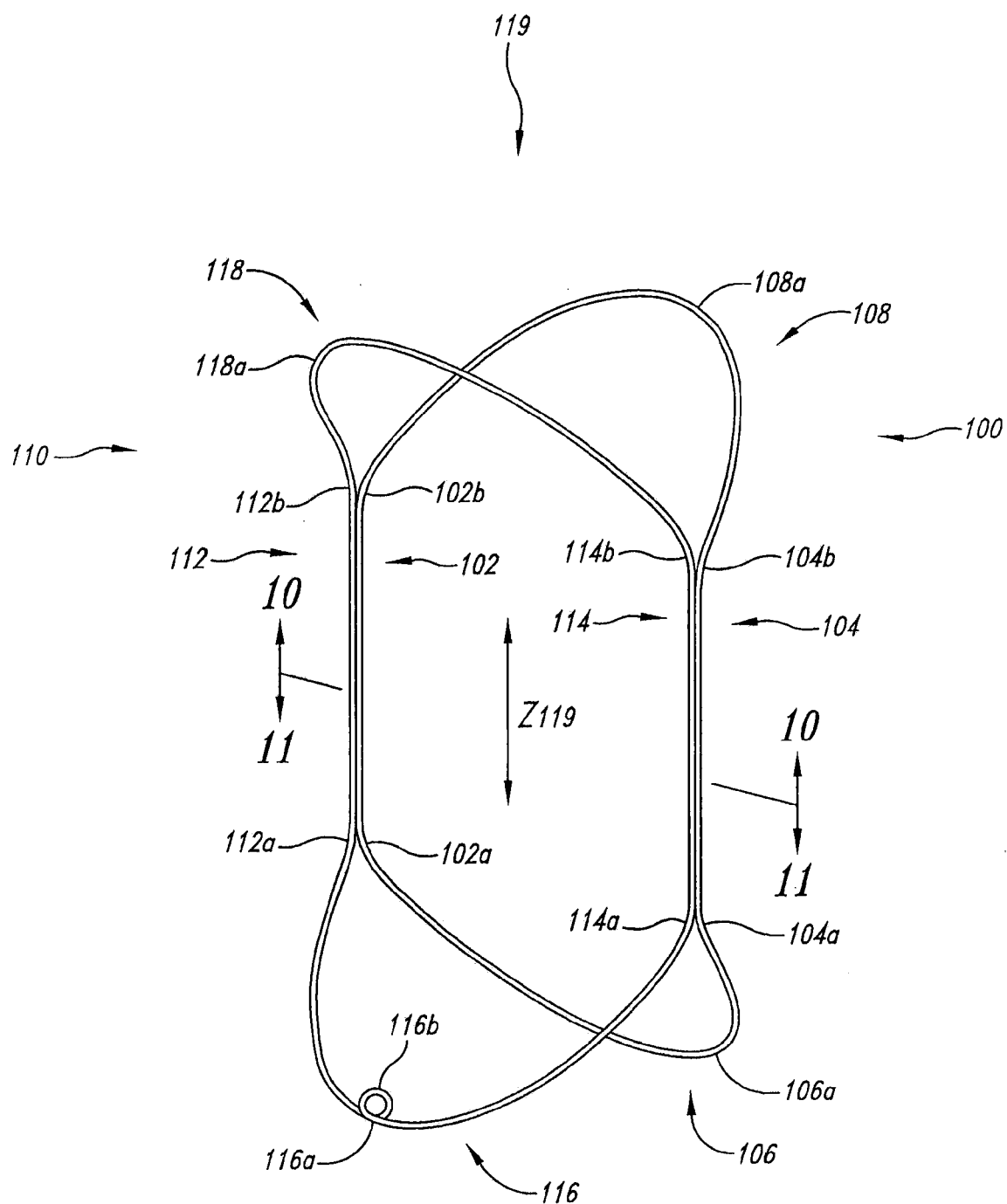
FIG. 9 is a perspective view of the first anchoring trunk member of the vascular anchoring system as having both the first anchoring trunk section and the second anchoring trunk section forming the first anchoring trunk member.

As shown in FIG. 9, the first anchoring trunk section 100 and the second anchoring trunk section 110 combine to form a first anchoring trunk member 119. The first longitudinal member 102 of the first anchoring trunk section 100 is integral with the first longitudinal member 112 of the second anchoring trunk section 110. The first apex 106a of the first anchoring trunk section 100 is spaced apart from the first apex 116a of the second anchoring trunk section 110. The second apex 108a of the first anchoring trunk section 100 is spaced apart from the second apex 118a of the second anchoring trunk section 110. Aspects include that the anchoring trunk member 119 be self-aligning when it is deployed into the vascular trunk 12. The anchoring trunk member 119 shown in FIG. 9 is self-aligning in yaw and pitch. Other aspects include that the anchoring trunk member 119 be self-expanding when it is deployed into the vascular trunk 12, to accommodate variations in vessel size and shape between individual subjects. Further aspects include that the anchoring trunk member 119 have a clear bore nearly as large as the vascular trunk into which it is deployed, to provide both for unobstructed fluid flow and to allow for passage of catheters, such as Swan-Ganz catheters, or other medical devices, that may be inserted into the vascular trunk.

Figure 10:
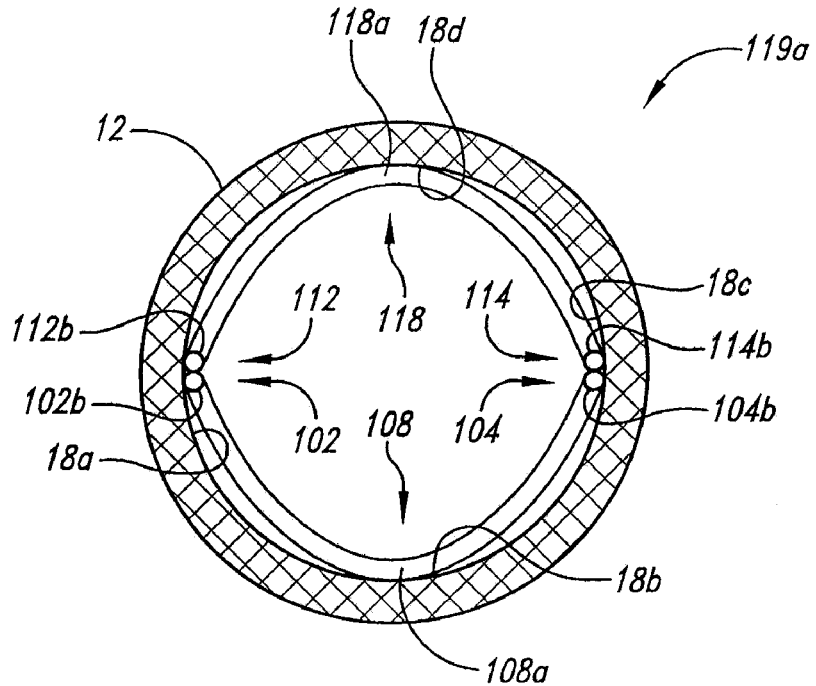
FIG. 10 is a sectional view of the first anchoring trunk member taken along the 10-10 line of FIG. 9 and a sectional view of the bifurcated vasculature taken along the 4-4 line of FIG. 1 with the first anchoring trunk member depicted as being inserted into the vascular trunk of the bifurcated vasculature.
Figure 11:
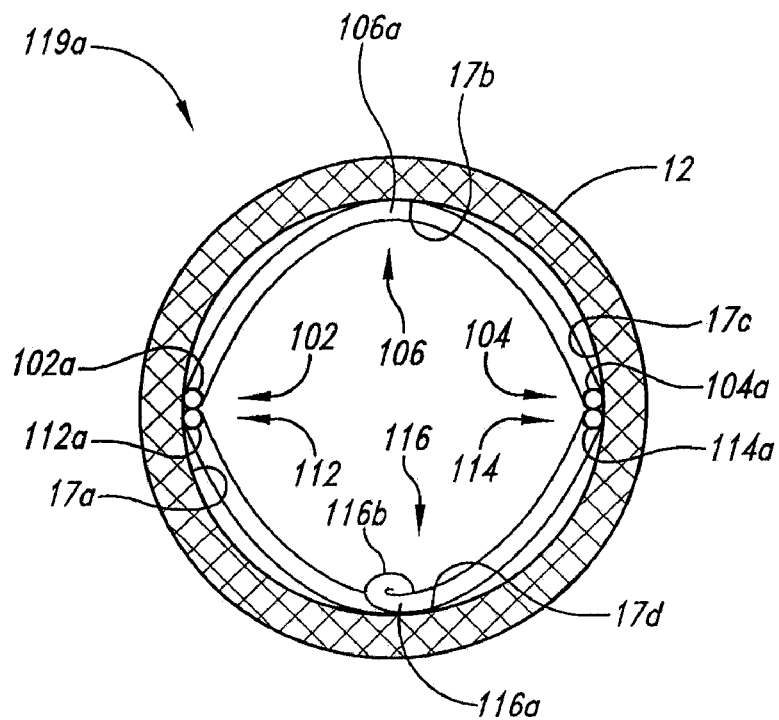
FIG. 11 is a sectional view of the first anchoring trunk member taken along the 10-10 line of FIG. 9 and a sectional view of the bifurcated vasculature taken along the 1B-1B line of FIG. 1 with the first anchoring trunk member depicted as being inserted into the vascular trunk of the bifurcated vasculature.

The first anchoring trunk member 119 is shown in FIG. 10 for illustration purposes as how the first anchoring trunk member would be positioned inside of the vascular trunk 12 in a first position 119a as a sectional view of the first anchoring trunk member taken along the 10-10 line of FIG. 9 and a sectional view of the bifurcated vasculature taken along the 4-4 line of FIG. 1. The first anchoring trunk member 119 is shown in FIG. 11 for illustration purposes as how the first anchoring trunk member would be positioned inside of the vascular trunk 12 in the first position 119a as a sectional view of the first anchoring trunk member taken along the 11-11 line of FIG. 9 and a sectional view of the bifurcated vasculature taken along the 1B-1B line of FIG. 1.

Figure 12:
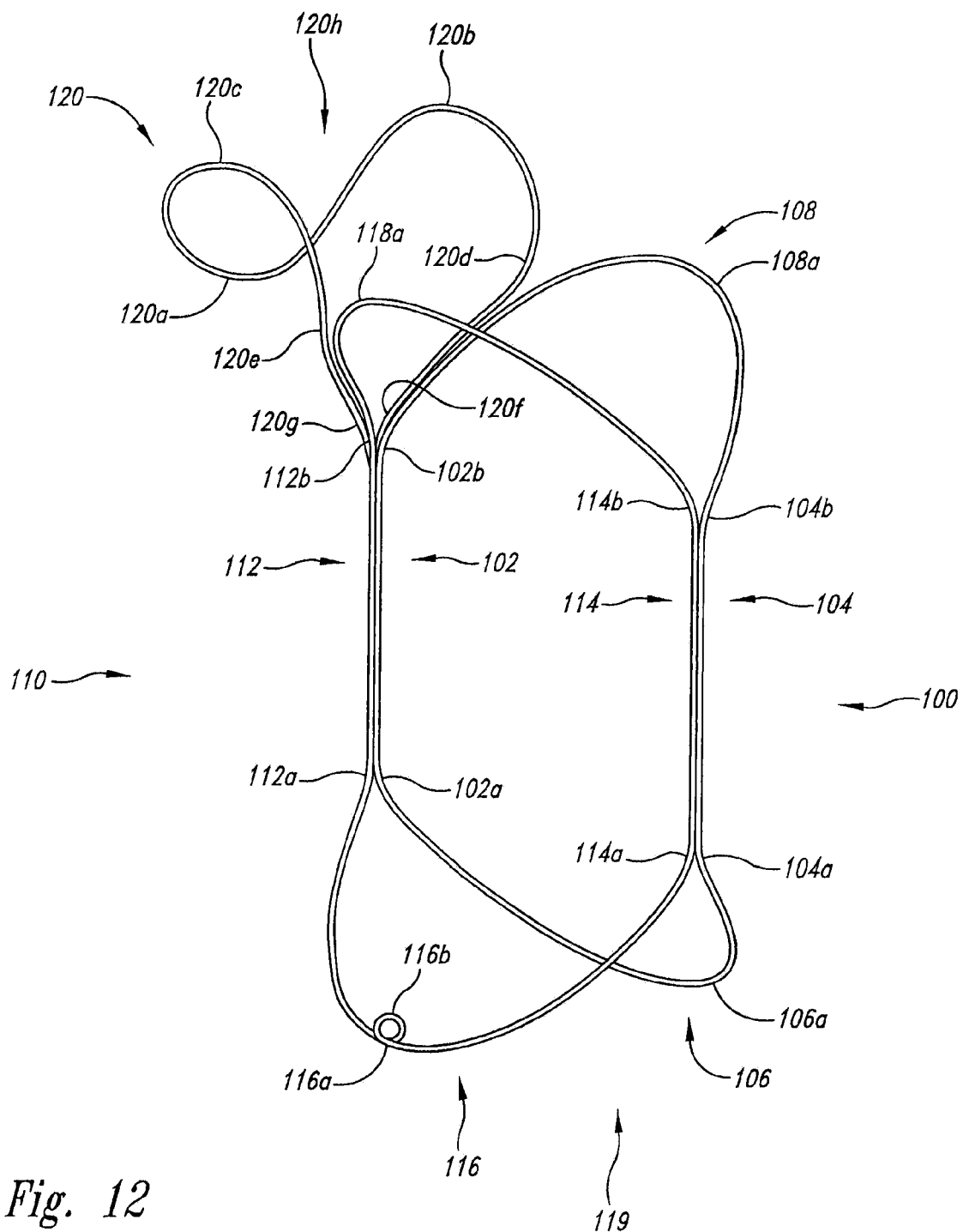
FIG. 12 is a perspective view of the first anchoring trunk member and a first anchoring branch member of the vascular anchoring system.

The first anchoring trunk member 119 is shown in FIG. 12 as integrated with a first anchoring branch member 120. The first anchoring branch member 120 has an end portion 120a, a first saddle side portion 120b, a second saddle side portion 120c, a first open side portion 120d, a second open side portion 120e, a first open end portion 120f, and a second open end portion 120g. The depicted first anchoring branch 120 is constructed as a frame structure to include the saddle end portion 120a, the first saddle side portion 120b, and the second saddle side portion 120c, which are integrally formed as a saddle-frame portion 120h shaped like an outline of a portion of a saddle surface of negative Gaussian curvature. The first anchoring trunk member 119 can stabilize an alignment with a vascular trunk or other such trunk for yaw and pitch movements, but a branch member, such as the first anchoring branch member 120, is needed for stabilizing alignment with a vascular trunk or other trunk for roll movements.

The first open side portion 120d extends from the first saddle side portion 120b to couple with the second convex arch 108 through the first open end portion 120f and thereby couples with the first longitudinal member 102 of the first anchoring trunk section 100. The second open side portion 120e extends from the second saddle side portion 120c to couple with the second convex arch 118 through the second open end portion 120g and thereby couples with the first longitudinal member 112 of the second anchoring trunk section 110.

Figure 13:
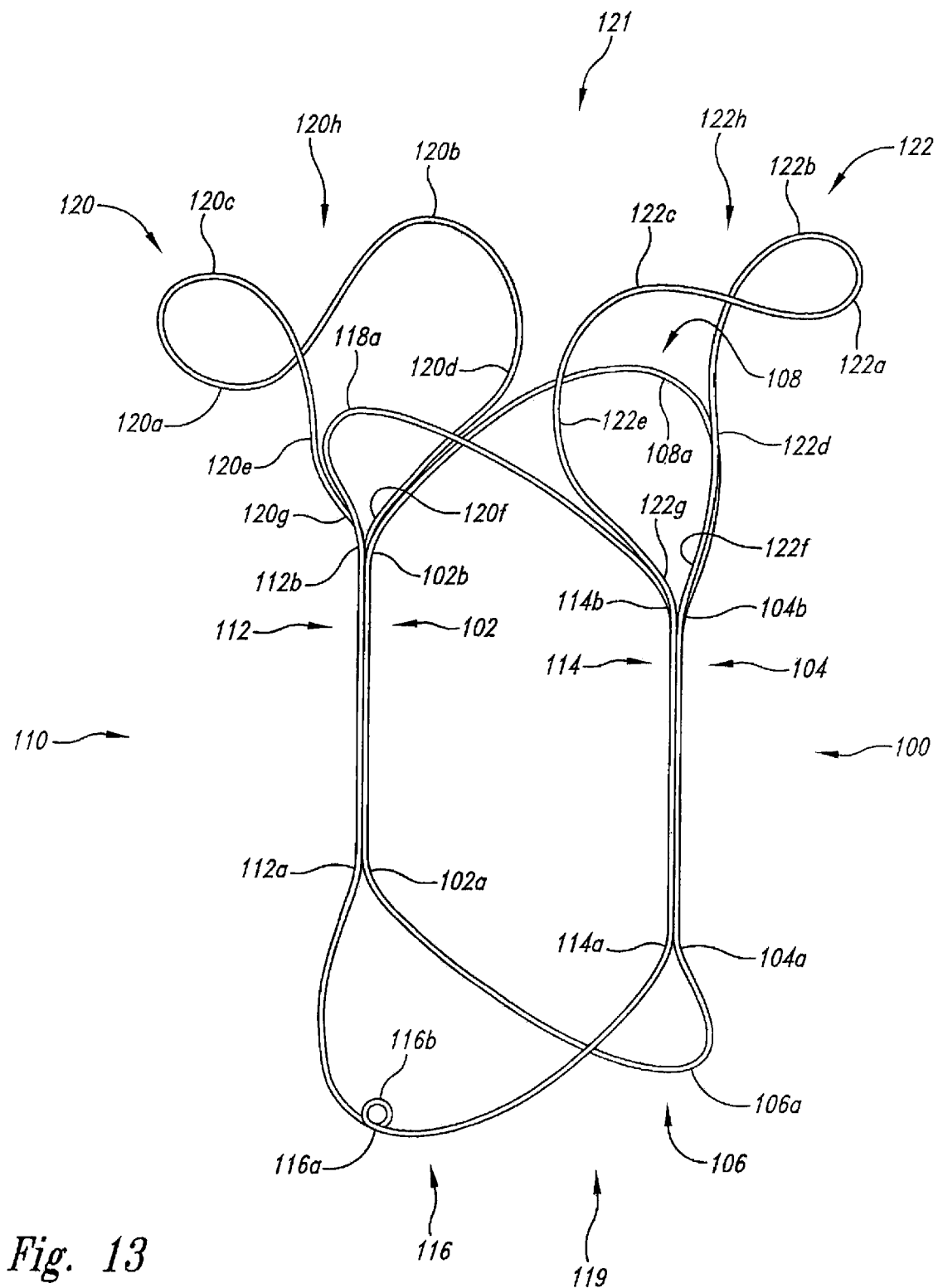
FIG. 13 is a perspective view of the vascular anchoring system showing both the first anchoring branch member and a second anchoring branch member.
Figure 13A:
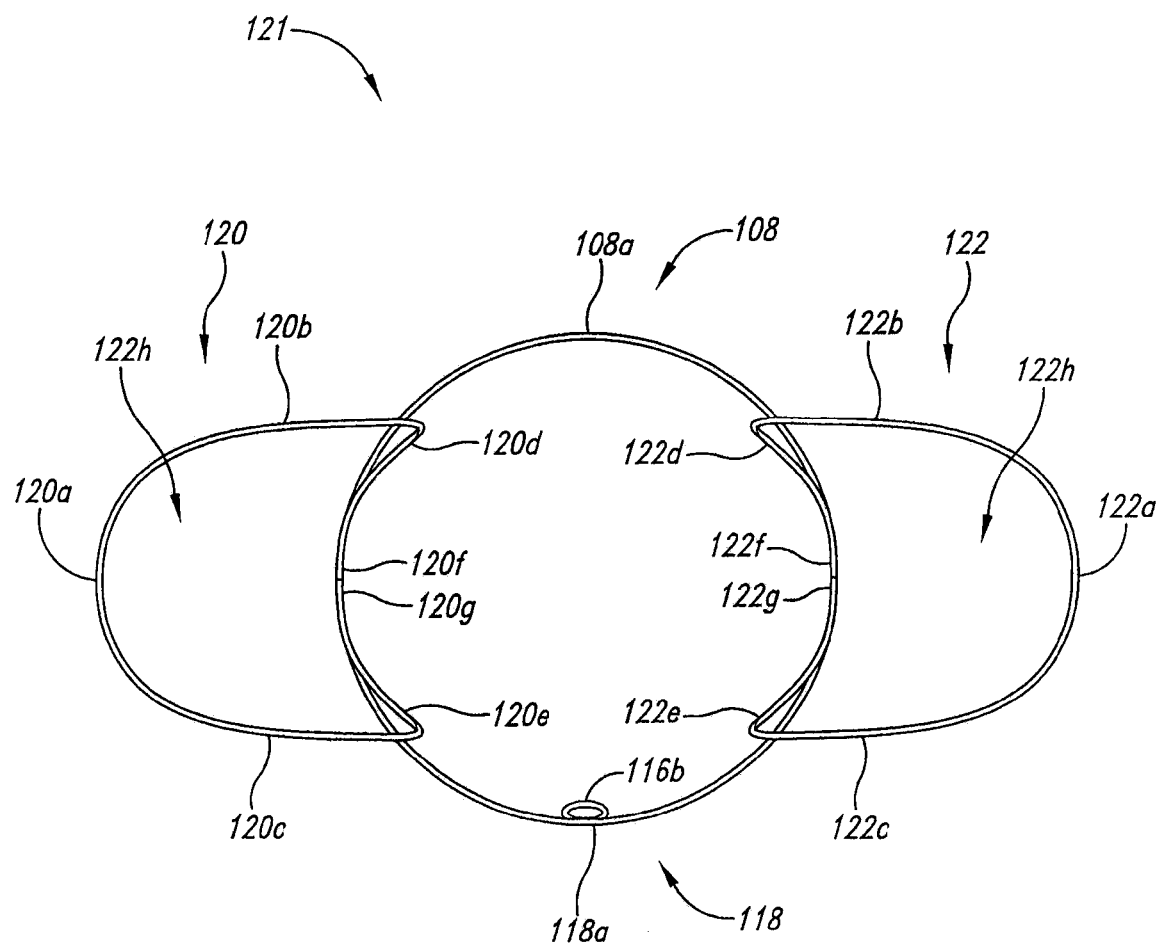
FIG. 13A is a top plan view of the vascular anchoring system.
Figure 13B:
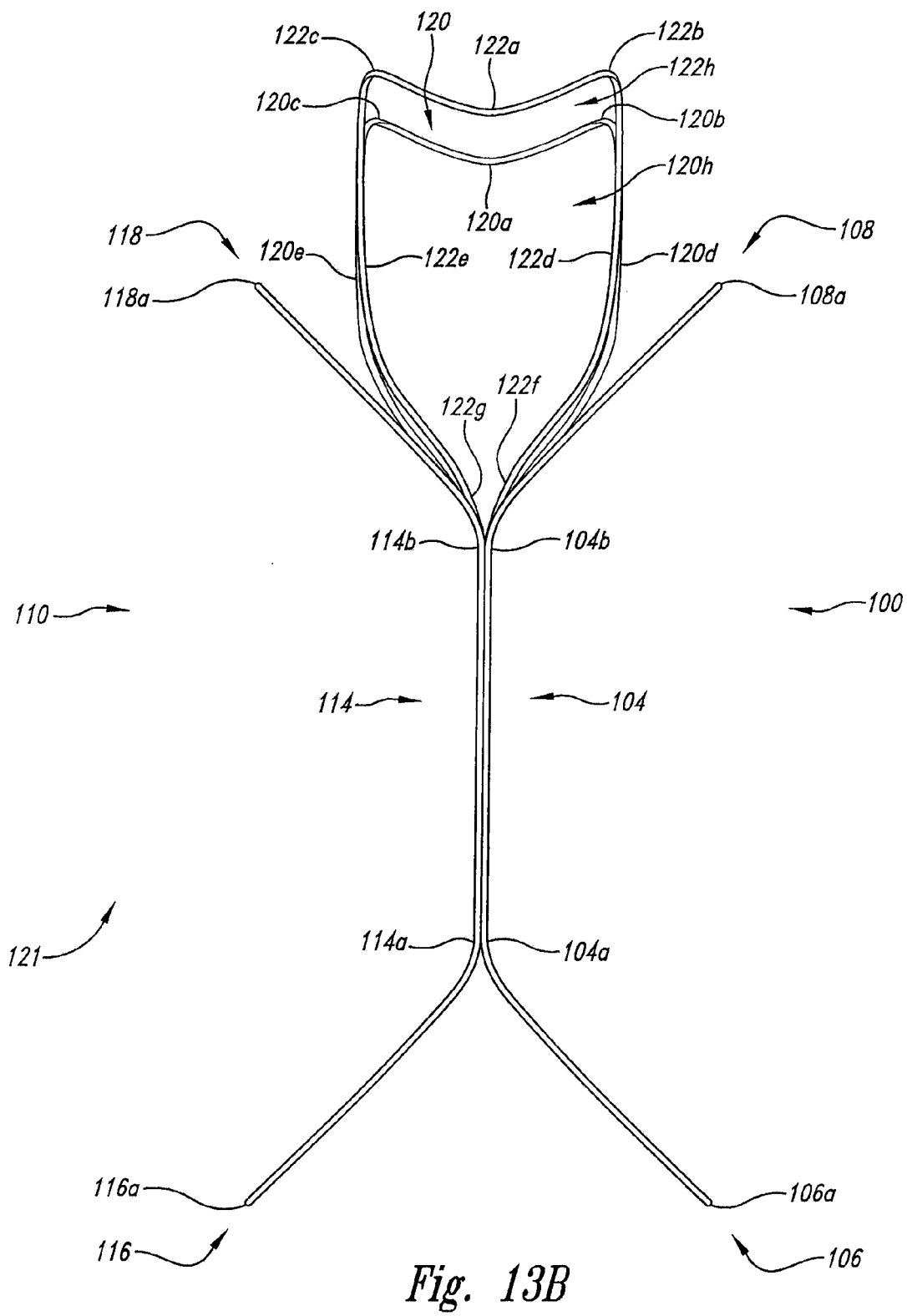
FIG. 13B is a side elevational view of the vascular system.

A first vascular anchoring system 121 is shown in FIGS. 13A and 13B and better shown in FIG. 13 as having the first anchoring trunk member 119 integrated with the first anchoring branch member 120 and a second anchoring branch member 122. The second anchoring branch member 122 has an end portion 122a, a first saddle side portion 122b, a second saddle side portion 122c, a first open side portion 122d, a second open side portion 122e, a first open end portion 122f, and a second open end portion 122g. The depicted first anchoring branch 122 is constructed as a frame structure to include the saddle end portion 122a, the first saddle side portion 122b, and the second saddle side portion 122c, which are integrally formed as a saddle-frame portion 122h shaped like an outline of a portion of a saddle surface of negative Gaussian curvature. Aspects include that the anchoring trunk member 121 be self-aligning when it is deployed into the vascular trunk 12. The anchoring trunk member 121 shown in FIG. 13 is self-aligning in yaw and pitch as a result of its anchoring trunk sections 100 and 110, and is self-aligning in roll and in axial location within the vascular trunk 12 as a result of its anchoring branch members 120 and 122.

The first open side portion 122d extends from the first saddle side portion 122b to couple with the second convex arch 108 through the first open end portion 122f and thereby couples with the second longitudinal member 104 of the first anchoring trunk section 100. The second open side portion 120e extends from the second saddle side portion 122c to couple with the second convex arch 118 through the second open end portion 122g and thereby couples with the second longitudinal member 114 of the second anchoring trunk section 110.

Figure 14:
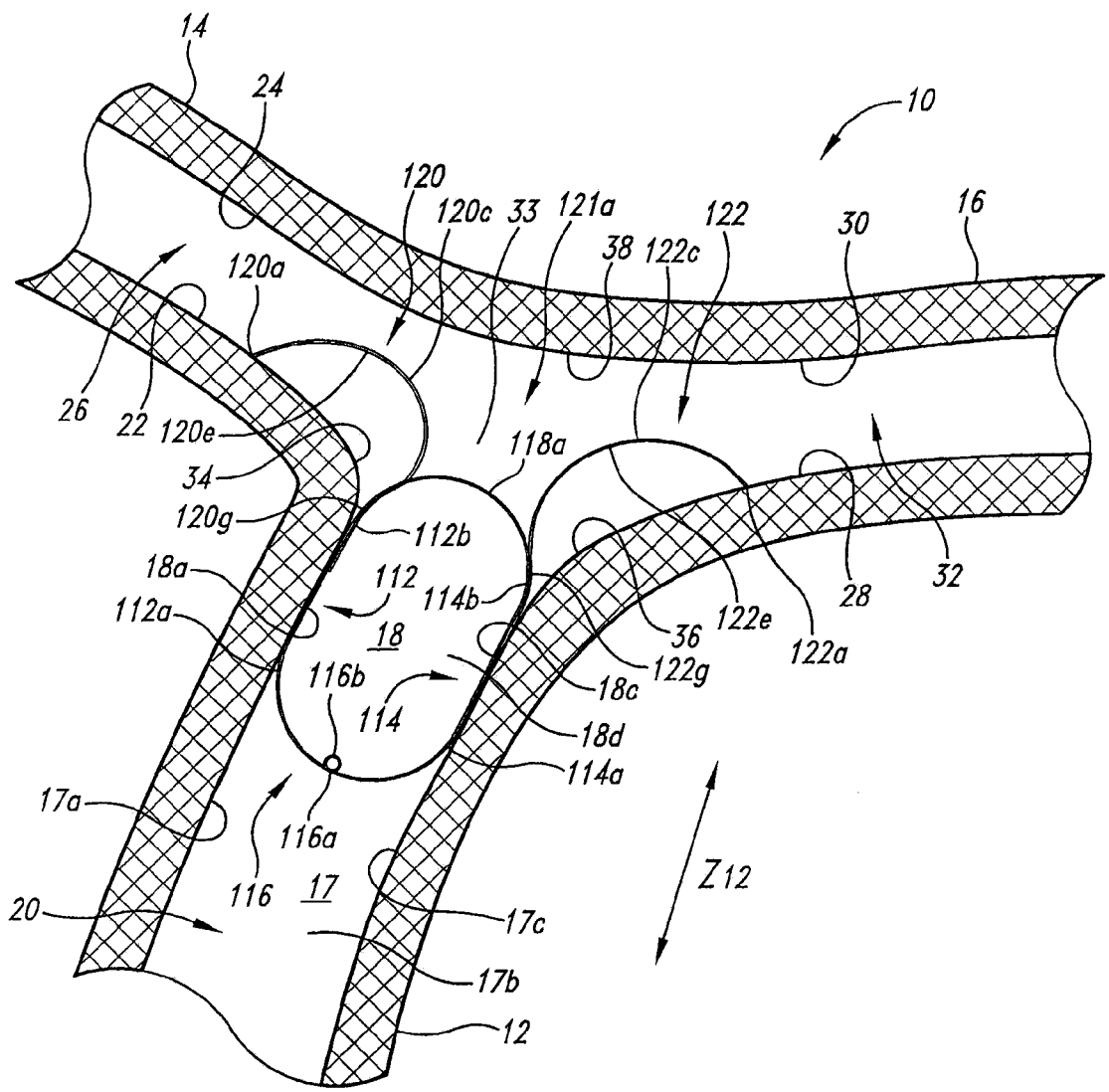
FIG. 14 is a front elevational view of the vascular anchoring system and a fragmented sectional view of the bifurcated vasculature of FIG. 1 taken along the 1A-1A line with the vascular anchoring system depicted as being inserted into the vascular trunk of the bifurcated vasculature.
Figure 15:
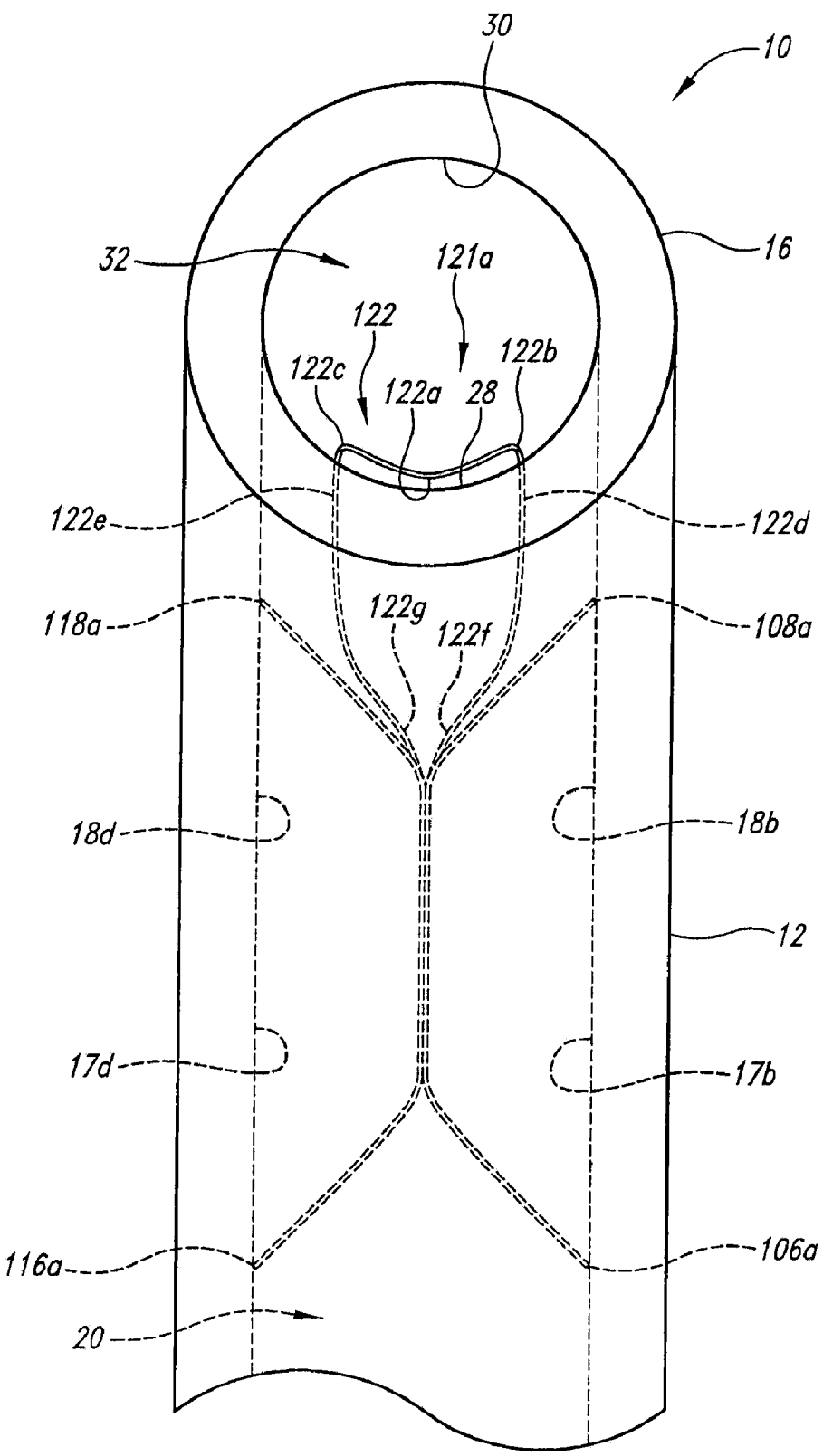
FIG. 15 is a side elevational view of the vascular anchoring system and a fragmented sectional view of the bifurcated vasculature of FIG. 1 taken along the 15-15 line with the vascular anchoring system depicted as being inserted into the vascular trunk of the bifurcated vasculature.

The first vascular anchoring system 121 is shown in FIGS. 14 and 15 being located in a first position 121a within the bifurcated vasculature 10. Fluid flow in the bifurcated vasculature 10 does not substantially effect positioning of the first vascular anchoring system 121 so has not been depicted in FIG. 14, FIG. 15, and following. The first anchoring branch member 120 is located generally within the first branch interior 26 of the first vascular branch 14. The saddle end portion 120a and parts of the first saddle side portion 120b and the second saddle side portion 120c of the saddle frame portion 120h of the second anchoring branch member 120 is adjacent the first branch proximate surface 22 of the first vascular branch 14.

In the first position 121a of the first vascular anchoring system 121, the first anchoring trunk member 119 is located in the first position 119a. The first anchoring branch member 120 is located generally within the first branch interior 26 of the first vascular branch 14. The saddle end portion 120a and parts of the first saddle side portion 120b and the second saddle side portion 120c of the saddle frame portion 120h of the second anchoring branch member 120 is adjacent the first branch proximate surface 22 of the first vascular branch 14.

The second anchoring branch member 122 is located generally within the second branch interior 32 of the second vascular branch 16. The saddle end portion 122a and parts of the first saddle side portion 122b and the second saddle side portion 122c of the saddle frame portion 122h of the second anchoring branch member 122 is adjacent the second branch proximate surface 28 of the second vascular branch 16.

Figure 16:
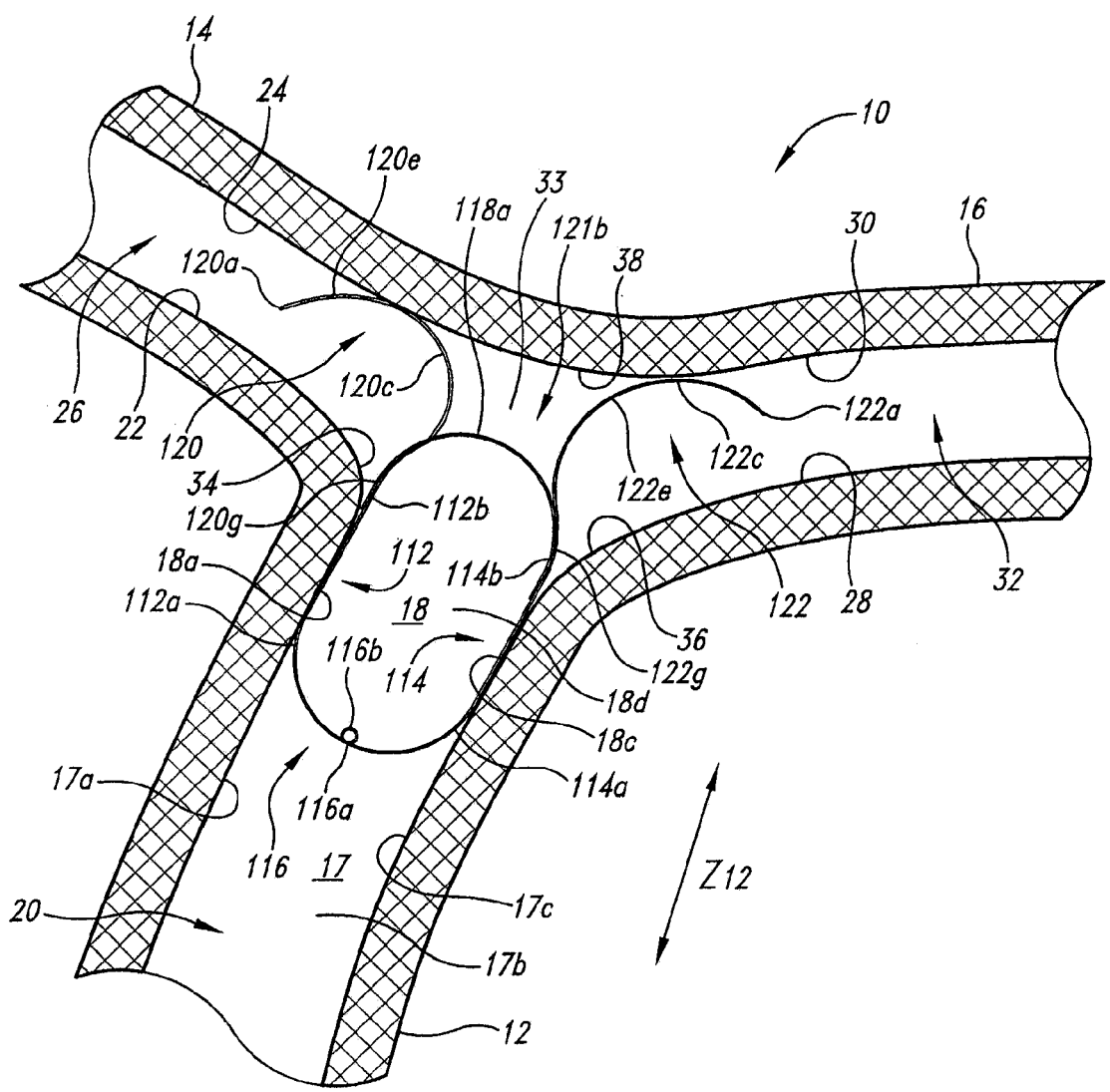
FIG. 16 is a front elevational view of the vascular anchoring system and a fragmented sectional view of the bifurcated vasculature of FIG. 1 taken along the 1A-1A line with the vascular anchoring system depicted as being inserted into the vascular trunk of the bifurcated vasculature.
Figure 17:
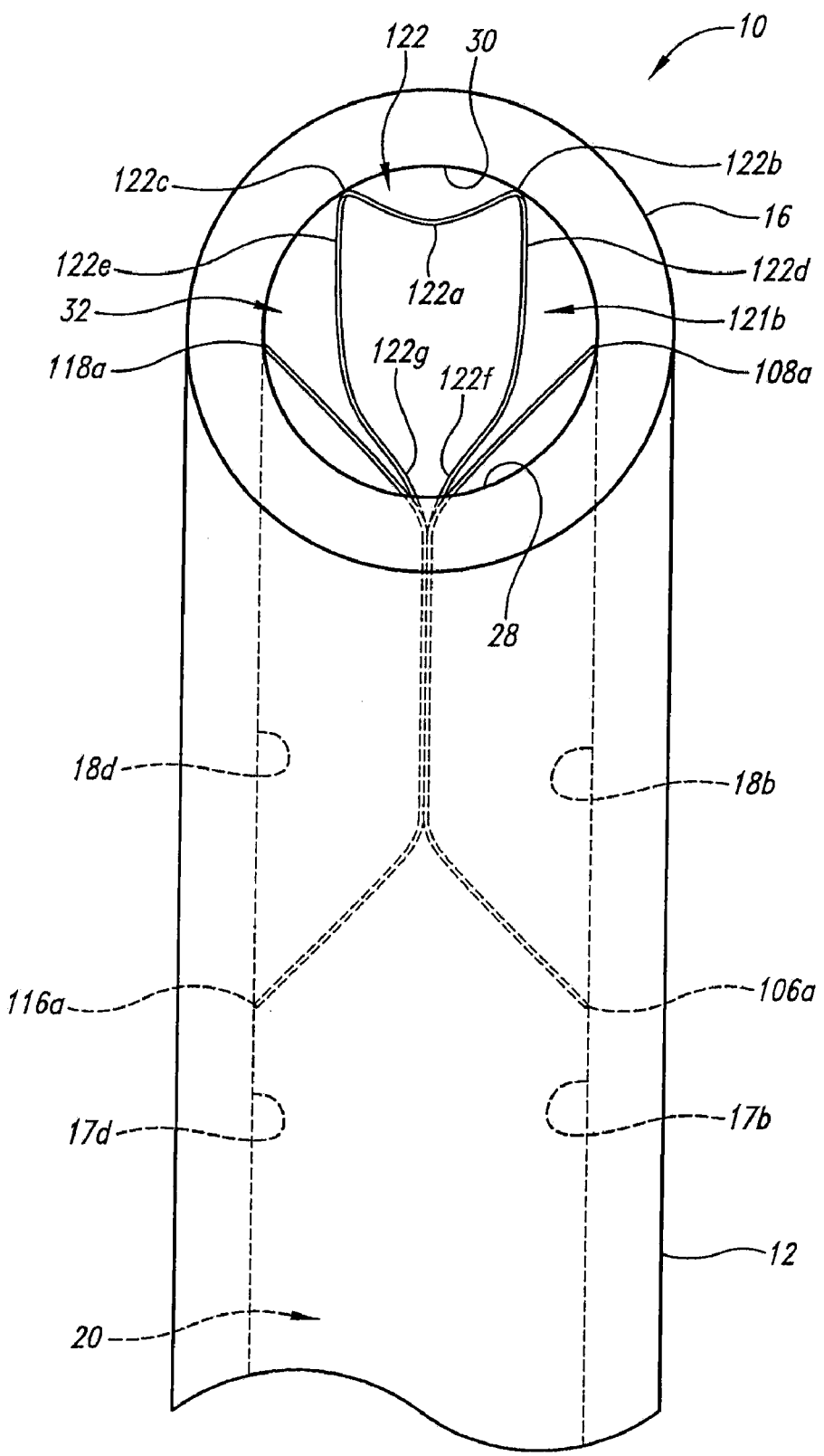
FIG. 17 is a side elevational view of the vascular anchoring system and a fragmented sectional view of the bifurcated vasculature of FIG. 1 taken along the 15-15 line with the vascular anchoring system depicted as being inserted into the vascular trunk of the bifurcated vasculature.

The first vascular anchoring system 121 is shown in FIGS. 16 and 17 as being located in a second position 121b within the bifurcated vasculature 10, which may be different than the first position 121a due to size differences between particular instances of the bifurcated vasculature 10 or size differences between particular instances of the first vascular anchoring system 121. In the second position 121b of the first vascular anchoring system 121, the first anchoring trunk member 119 is shifted slightly relative to the first position 119a to be partially positioned into the intersection 33 of the bifurcated vasculature 10. The first saddle side portion 120b and the second saddle side portion 120c of the first anchoring branch member 120 and the first saddle side portion 122b and the second saddle side portion 122c of the second anchoring branch member 122 are shown as touching the first branch distal surface 24 and the second branch distal surface 30, respectively.

Figure 18:
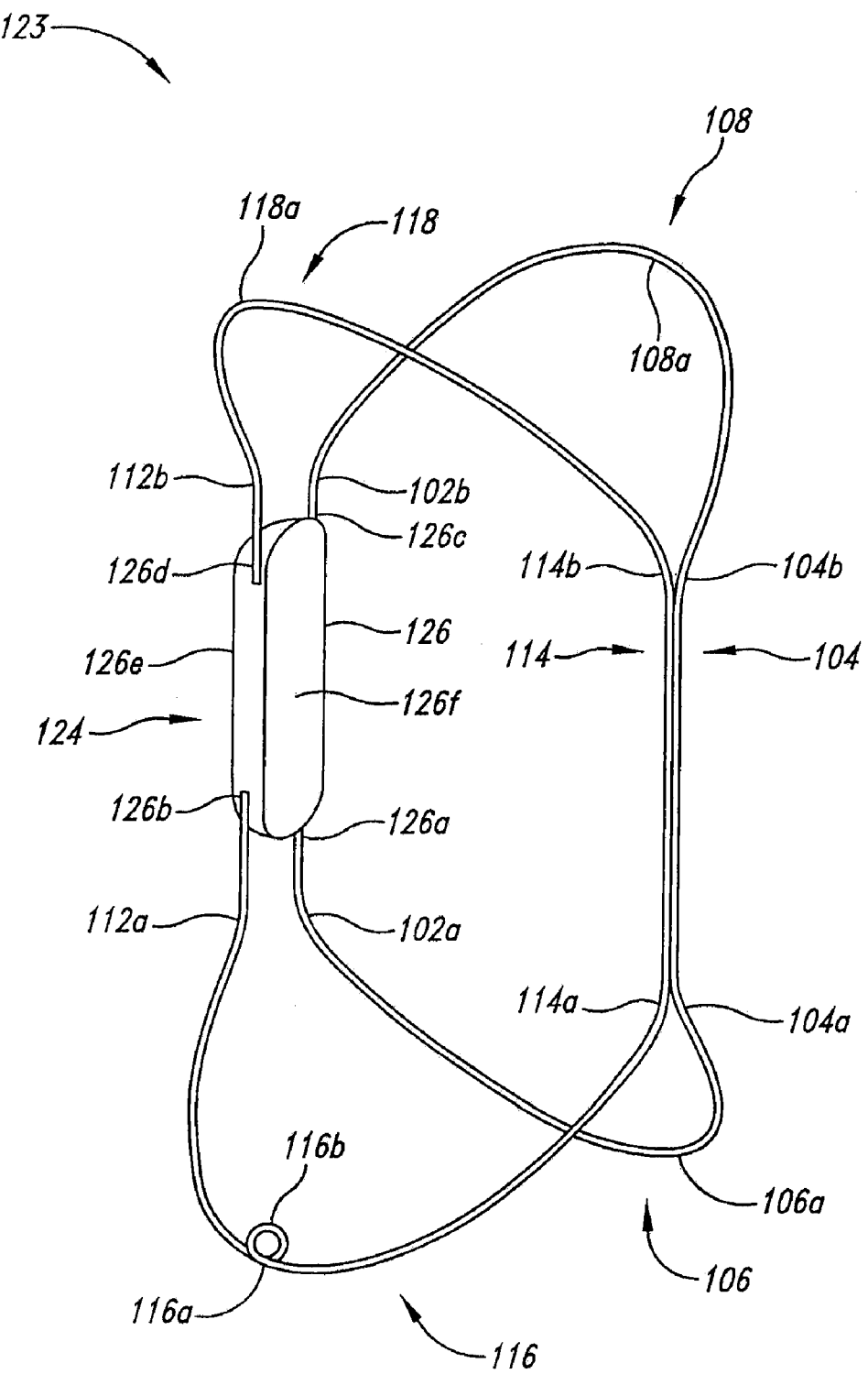
FIG. 18 is a perspective view of a second anchoring trunk member including a first component package.
Figure 18A:
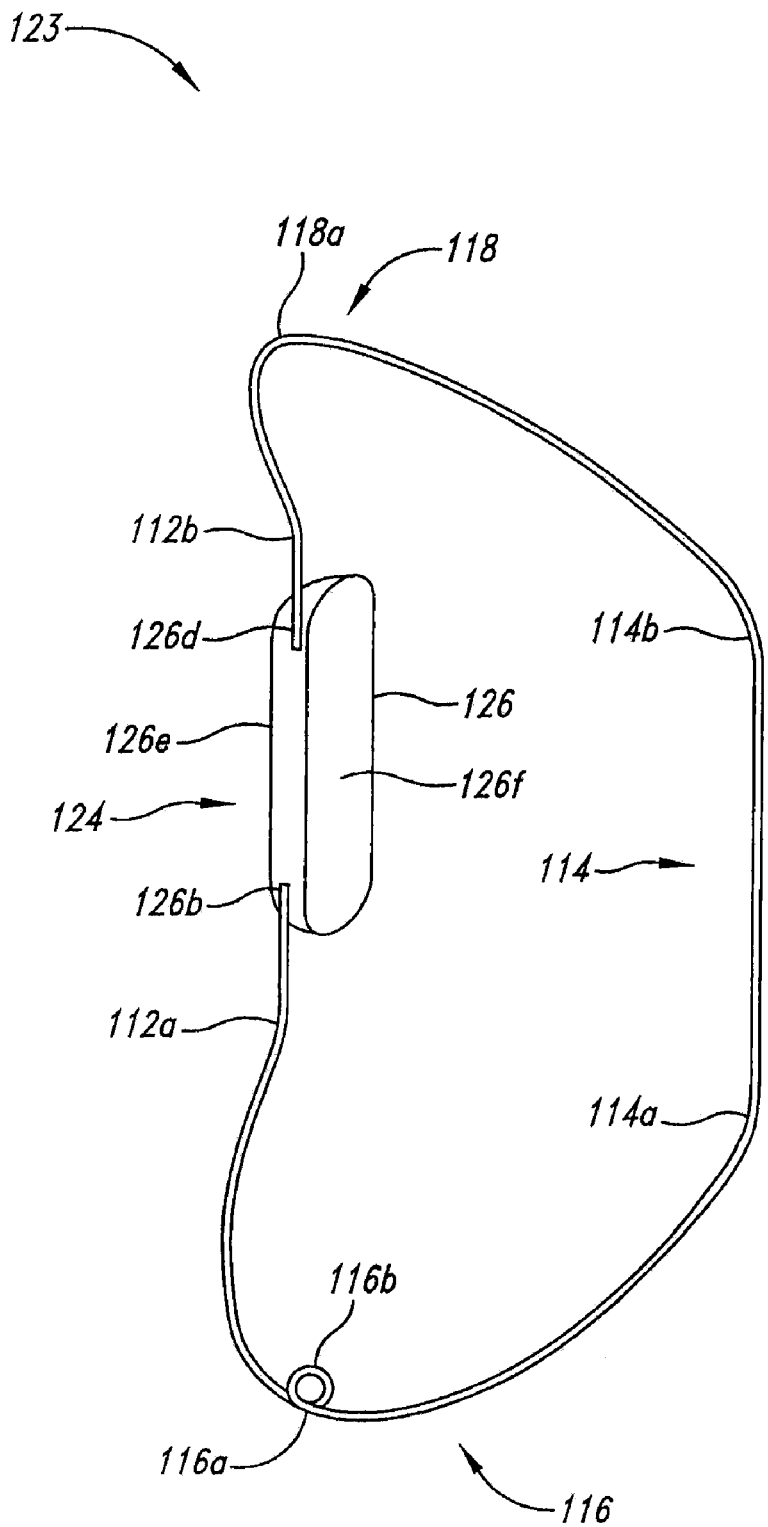
FIG. 18A is a perspective view of the exemplary second of the pair of the two anchoring sections of the first anchoring trunk member of the vascular anchoring system with the first component package.

A second anchoring trunk member 123 is shown in FIG. 18 as having a first component package 124 with a first elongated enclosure 126 having a first attachment point 126a, a second attachment point 126b, a third attachment point 126c, a fourth attachment point 126d, an outward facing exterior surface 126e, and an inward facing exterior surface 126f. For the second anchoring trunk member 123, the first longitudinal member 102 of the first anchoring trunk section 100 engages with the first elongated enclosure 126 at the first attachment point 126a and the third attachment point 126c near the first end 102a and the second end 102b, respectively. In some implementations, the first longitudinal member 102 can extend the length of the first elongated enclosure 126 whereas in other implementations, the first longitudinal member 102 can include two pieces with the first elongated enclosure extending therebetween. Some implementations only use a portion of the second anchoring trunk member 123 as shown in FIG. 18A having the exemplary second of the pair of the two anchoring sections of the first anchoring trunk member 119 and the first component package 124.

Figure 19:
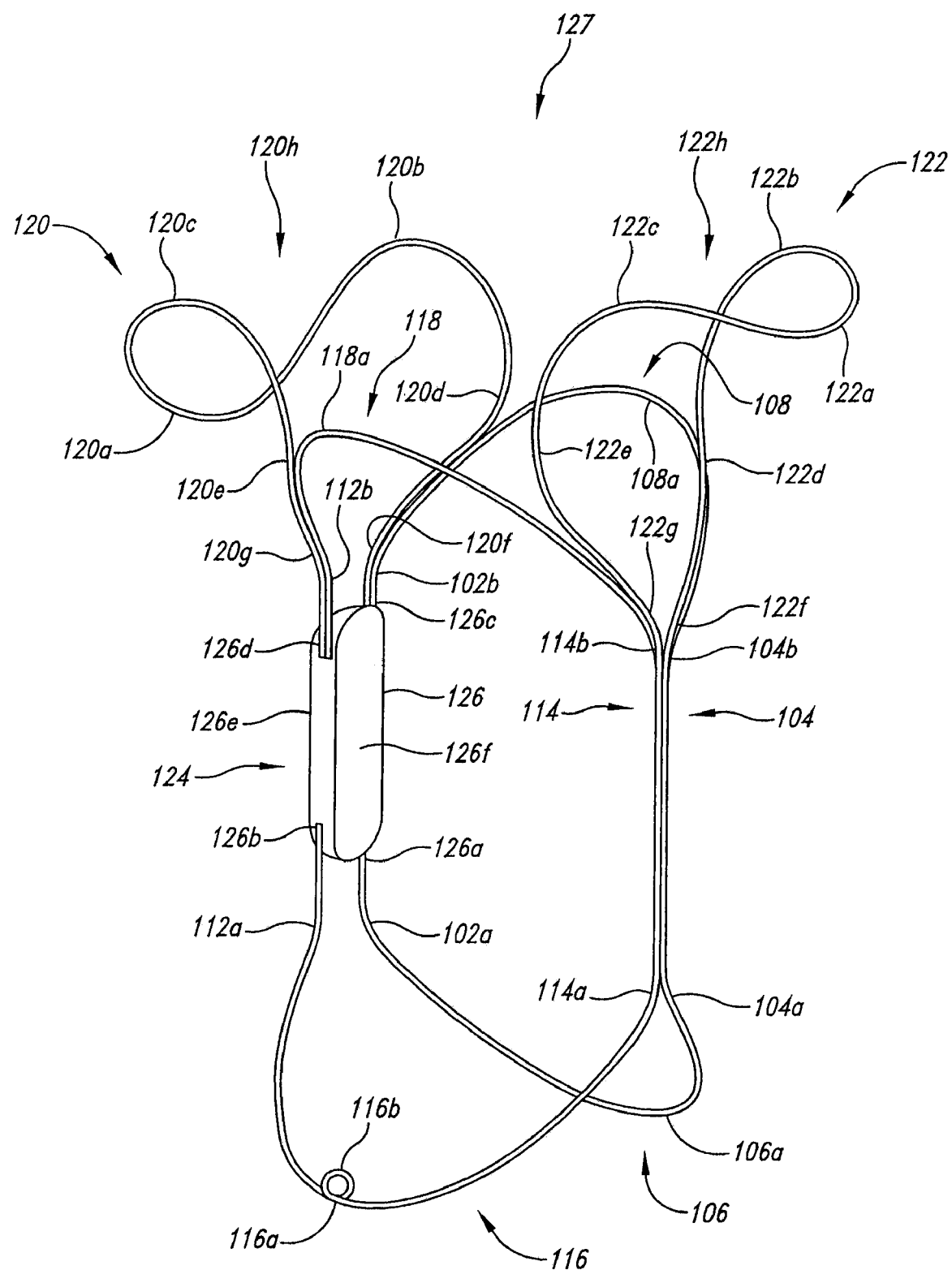
FIG. 19 is a perspective view of a second vascular anchoring system having the second anchoring trunk member of FIG. 18 with the first component package.

The first longitudinal member 112 of the second anchoring trunk section 110 engages with the first elongated enclosure 126 at the second attachment point 126b and the fourth attachment point 126d near the first end 112a and the second end 112b, respectively. In some implementations, the first longitudinal member 112 can extend the length of the first elongated enclosure 126 whereas in other implementations, the first longitudinal member 112 can include two pieces with the first elongated enclosure extending therebetween. The second anchoring trunk member 123 is shown in FIG. 19 as being integrated with the first anchoring branch member 120 and the second anchoring branch member 122 as a second vascular anchoring system 127 in a manner similar to that described above for the first vascular anchoring system 121.

Figure 20:
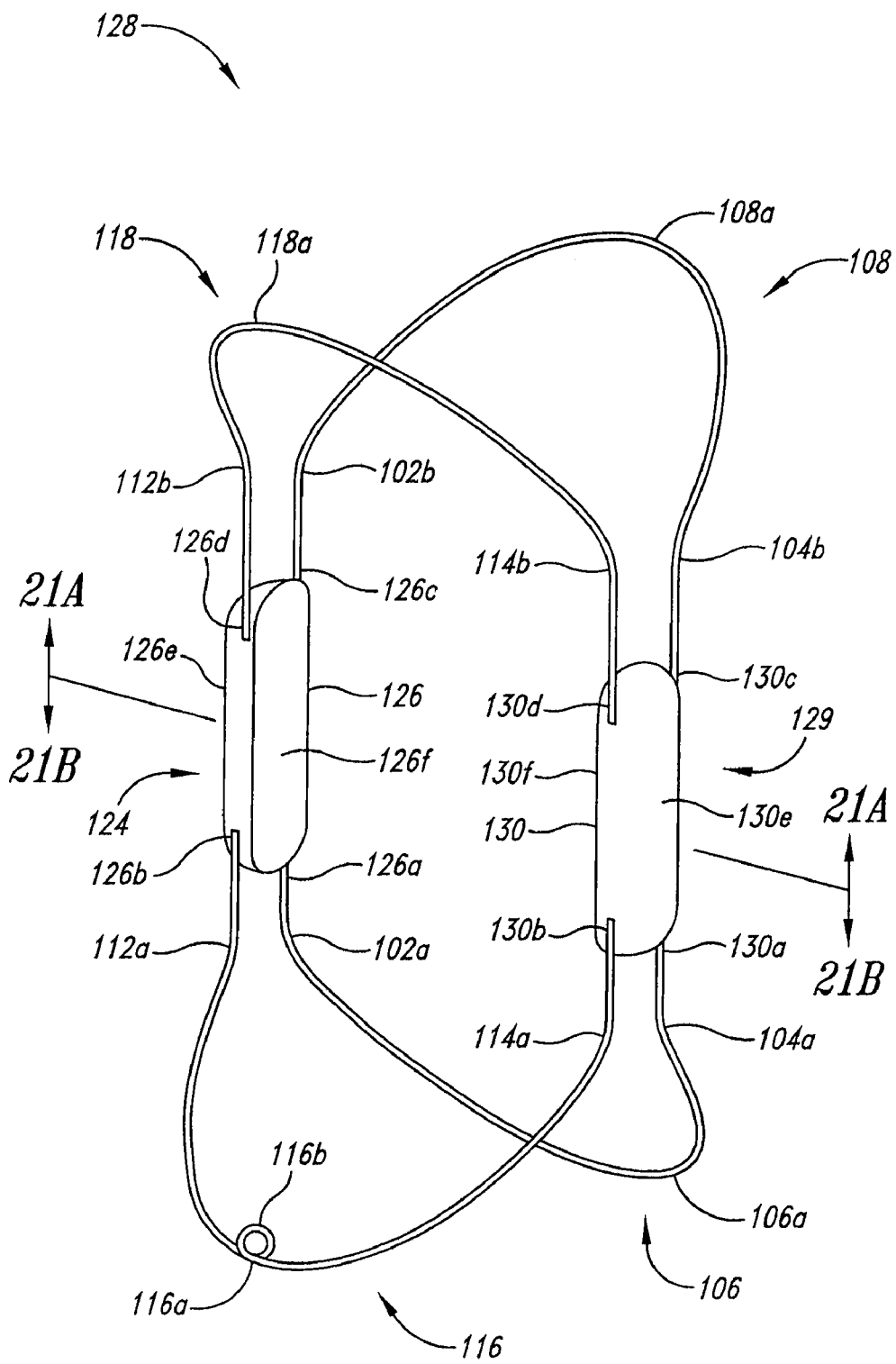
FIG. 20 is a perspective view of a third anchoring trunk member including the first component package and the second component package.
Figure 20A:
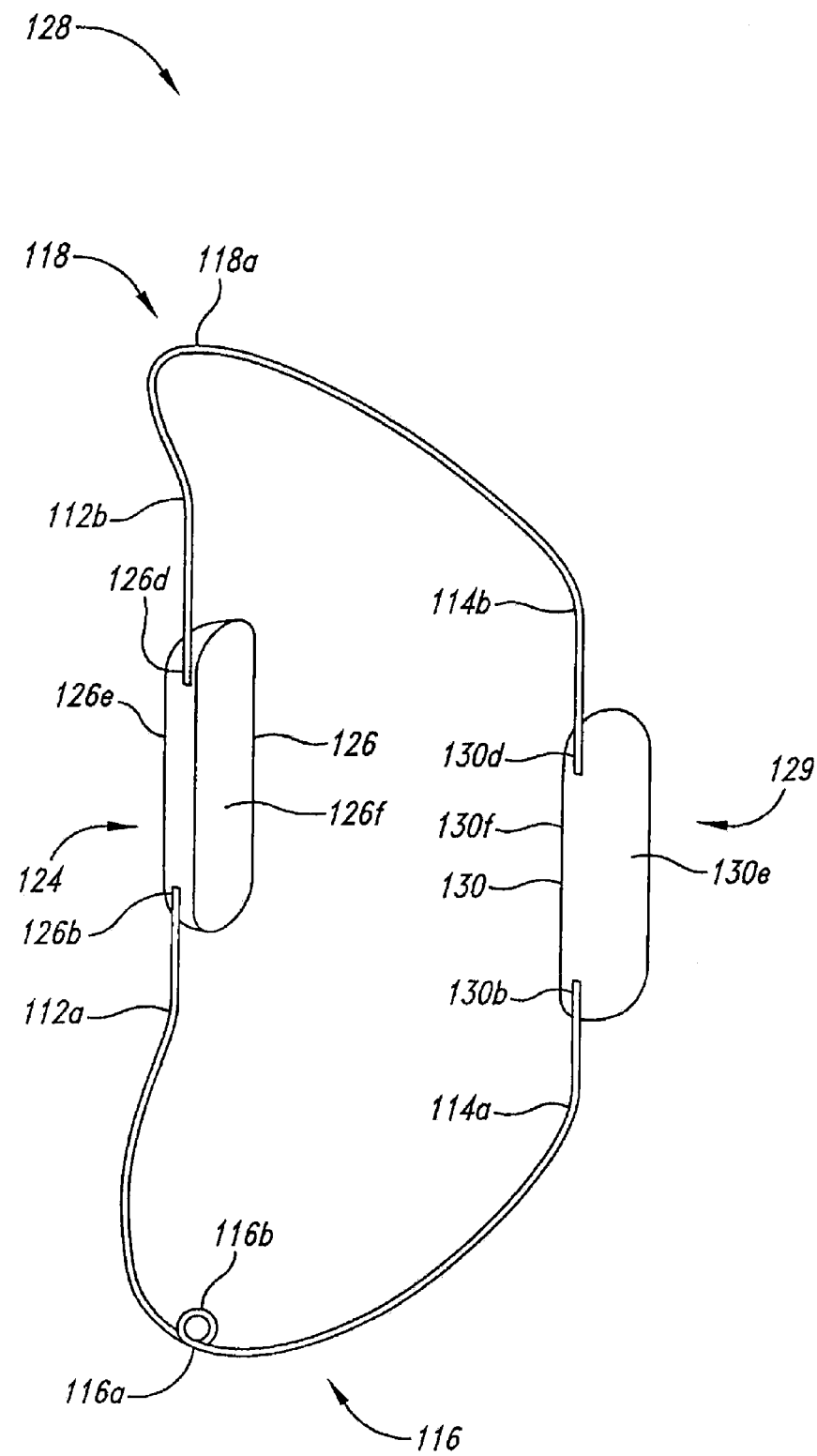
FIG. 20A is a perspective view of the exemplary second of the pair of the two anchoring sections of the first anchoring trunk member of the vascular anchoring system with the first component package and the second component package.

A third anchoring trunk member 128 is shown in FIG. 20 as having the first component package 124 and a second component package 129 with a second elongated enclosure 130 having a first attachment point 130a, a second attachment point 130b, a third attachment point 130c, and a fourth attachment point 130d, an outward facing exterior surface 130e, and an inward facing exterior surface 130f. For the third anchoring trunk member 128, the second longitudinal member 104 of the first anchoring trunk section 100 engages with the second elongated enclosure 130 at the first attachment point 130a and the third attachment point 130c near the first end 104a and the second end 104b, respectively. Some implementations only use a portion of the third anchoring trunk member 128 as shown in FIG. 20A having the exemplary second of the pair of the two anchoring sections of the first anchoring trunk member 119 and the first component package 124 and the second component package 129.

In some implementations, the second longitudinal member 104 can extend the length of the second elongated enclosure 130 whereas in other implementations, the second longitudinal member 104 can include two pieces with the second elongated enclosure extending therebetween. The second longitudinal member 114 of the second anchoring trunk section 110 engages with the second elongated enclosure 130 at the second attachment point 130b and the fourth attachment point 130d near the first end 114a and the second end 114b, respectively. In some implementations, the second longitudinal member 104 can extend the length of the second elongated enclosure 130 whereas in other implementations, the second longitudinal member 104 can include two pieces with the second elongated enclosure extending therebetween.

Figure 21A:
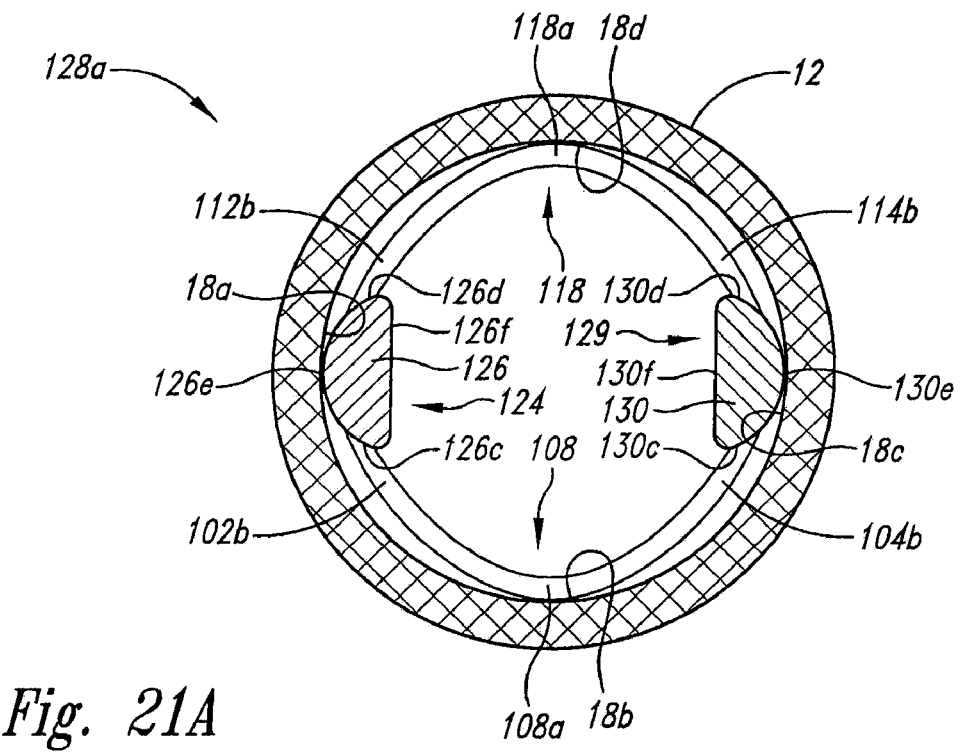
FIG. 21A is a sectional view of the third anchoring trunk member taken along the 21A-21A line of FIG. 20 and a sectional view of the bifurcated vasculature taken along the 4-4 line of FIG. 1 with the third anchoring trunk member depicted as being inserted into the vascular trunk of the bifurcated vasculature.

The third anchoring trunk member 128 is shown in FIG. 21A for illustration purposes as how the first anchoring trunk member would be positioned inside of the vascular trunk 12 in a first position 128a as a sectional view of the third anchoring trunk member taken along the 21A-21A line of FIG. 20 and a sectional view of the bifurcated vasculature taken along the 4-4 line of FIG. 1. As shown in FIG. 21A, portions of the first longitudinal member 102 and the second longitudinal member 104 of the of the first anchoring trunk section 100, portions of the first longitudinal member 112 and the second longitudinal member 114 of the second anchoring trunk section 110, the outward surface 126e of the first elongated enclosure 126, and the outward surface 130e of the second elongated enclosure 126 extend along the distal trunk surface portion 17 and the proximate trunk surface portion 18. The second convex arch 118 is shaped to substantially abut adjacent to the vascular trunk 12 extending substantially from the first proximate surface location 18a (where the second end 112b of the first longitudinal member 112 would be positioned) through the fourth proximate surface location 18d (where the second apex 118a would be positioned) on to the third proximate surface location 18c (where the second end 114b of the second longitudinal member 114 would be positioned).

Figure 21B:
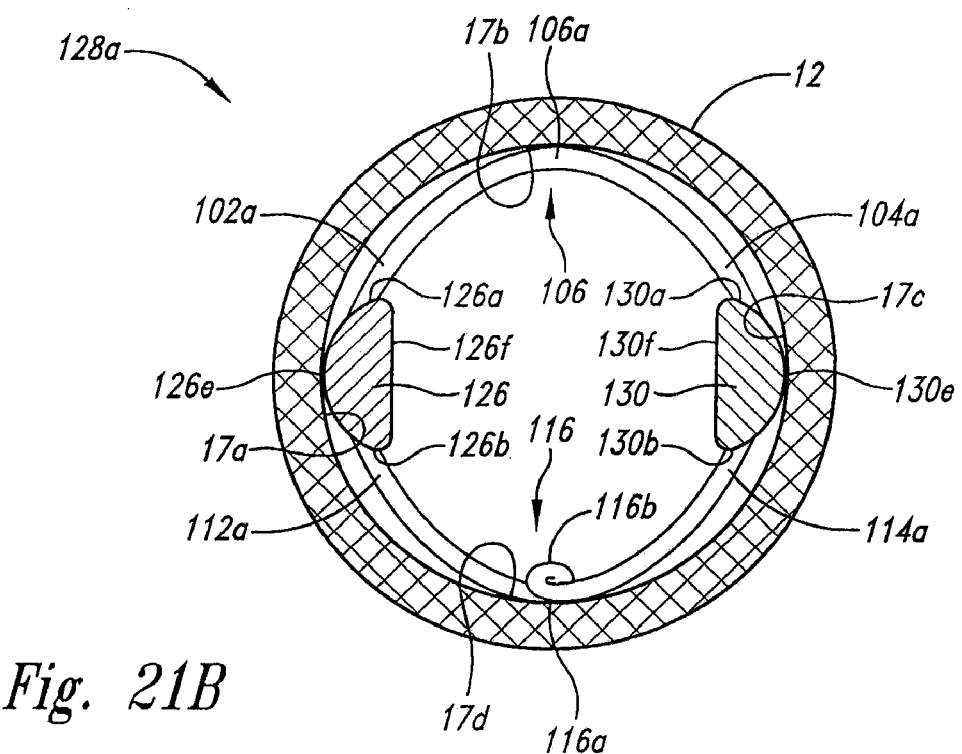
FIG. 21B is a sectional view of the third anchoring trunk member taken along the 21B-21B line of FIG. 20 and a sectional view of the bifurcated vasculature taken along the 1B-1B line of FIG. 1 with the third anchoring trunk member depicted as being inserted into the vascular trunk of the bifurcated vasculature.

The third anchoring trunk member 128 is shown in FIG. 21B for illustration purposes as how the first anchoring trunk member would be positioned inside of the vascular trunk 12 in the first position 128a as a sectional view of the first anchoring trunk member taken along the 21B-21B line of FIG. 20 and a sectional view of the bifurcated vasculature taken along the 1B-1B line of FIG. 1. As shown in FIG. 21B, the first convex arch 116 is shaped to substantially abut adjacent to the vascular trunk 12 extending substantially from the first distal surface location 17a (where the first end 112a of the first longitudinal member 112 would be positioned) through the fourth distal surface location 17d (where the first apex 116a would be positioned) on to the third distal surface location 17c (where the first end 114a of the second longitudinal member 114 would be positioned).

Figure 22:
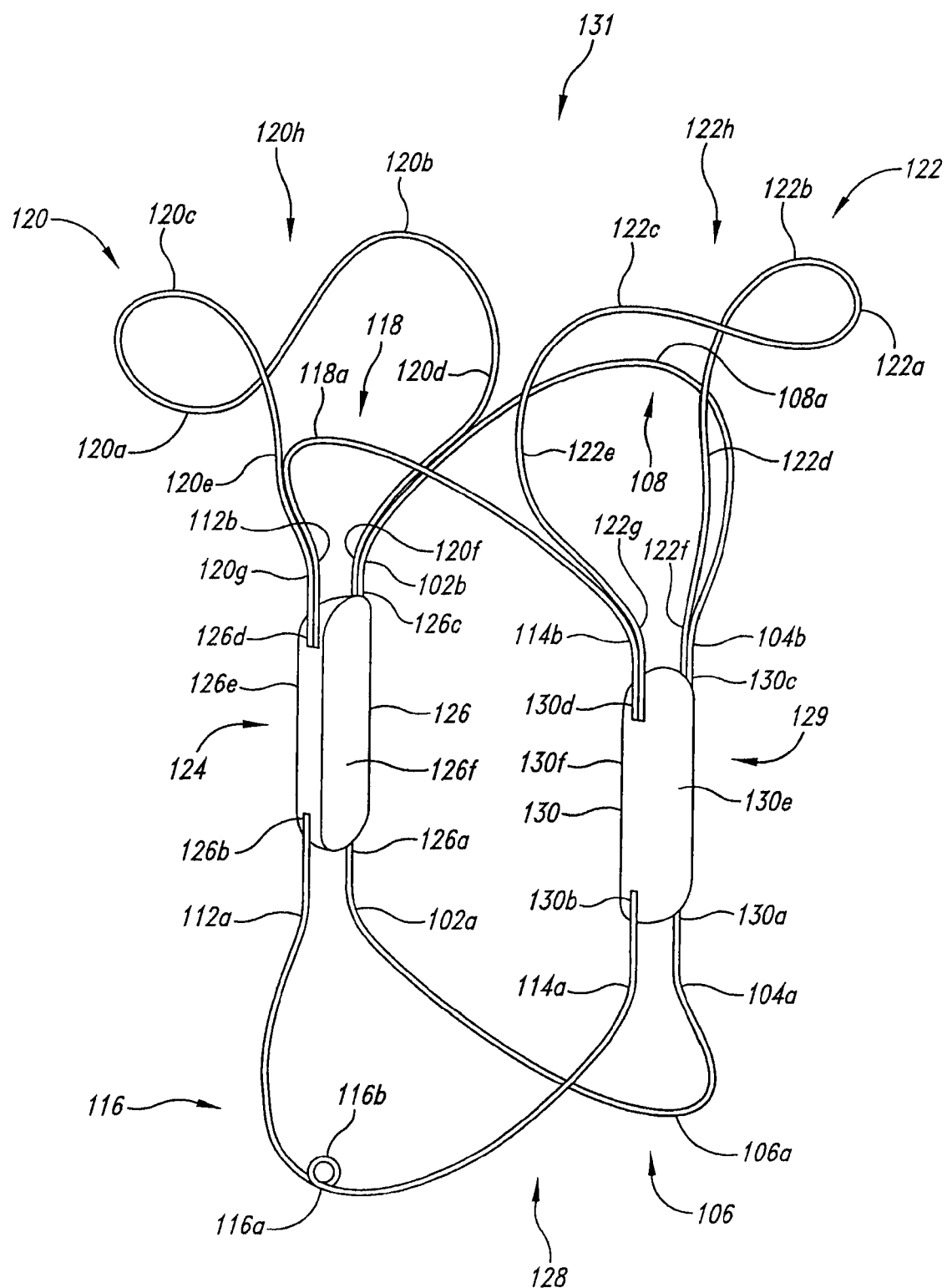
FIG. 22 is a perspective view of a third vascular anchoring system having the third anchoring trunk member of FIG. 20 with the first component package and the second component package.
Figure 23:
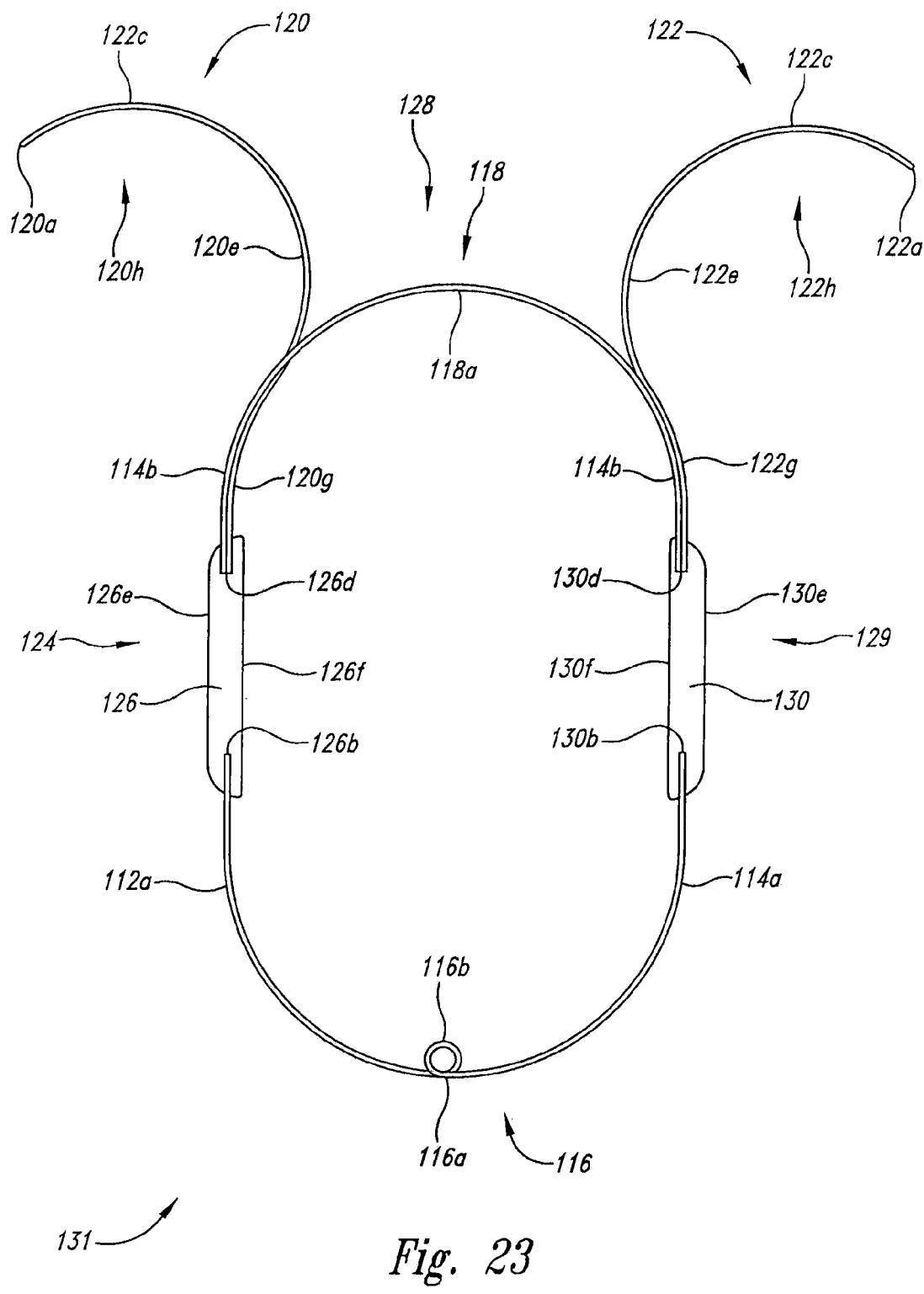
FIG. 23 is a front elevational view of the third vascular anchoring system version.

The third anchoring trunk member 128 is shown in FIGS. 22 and 23 as being integrated with the first anchoring branch member 120 and the second anchoring branch member 122 as a third vascular anchoring system 131 in a manner similar to the first vascular anchoring system 127.

Figure 24:
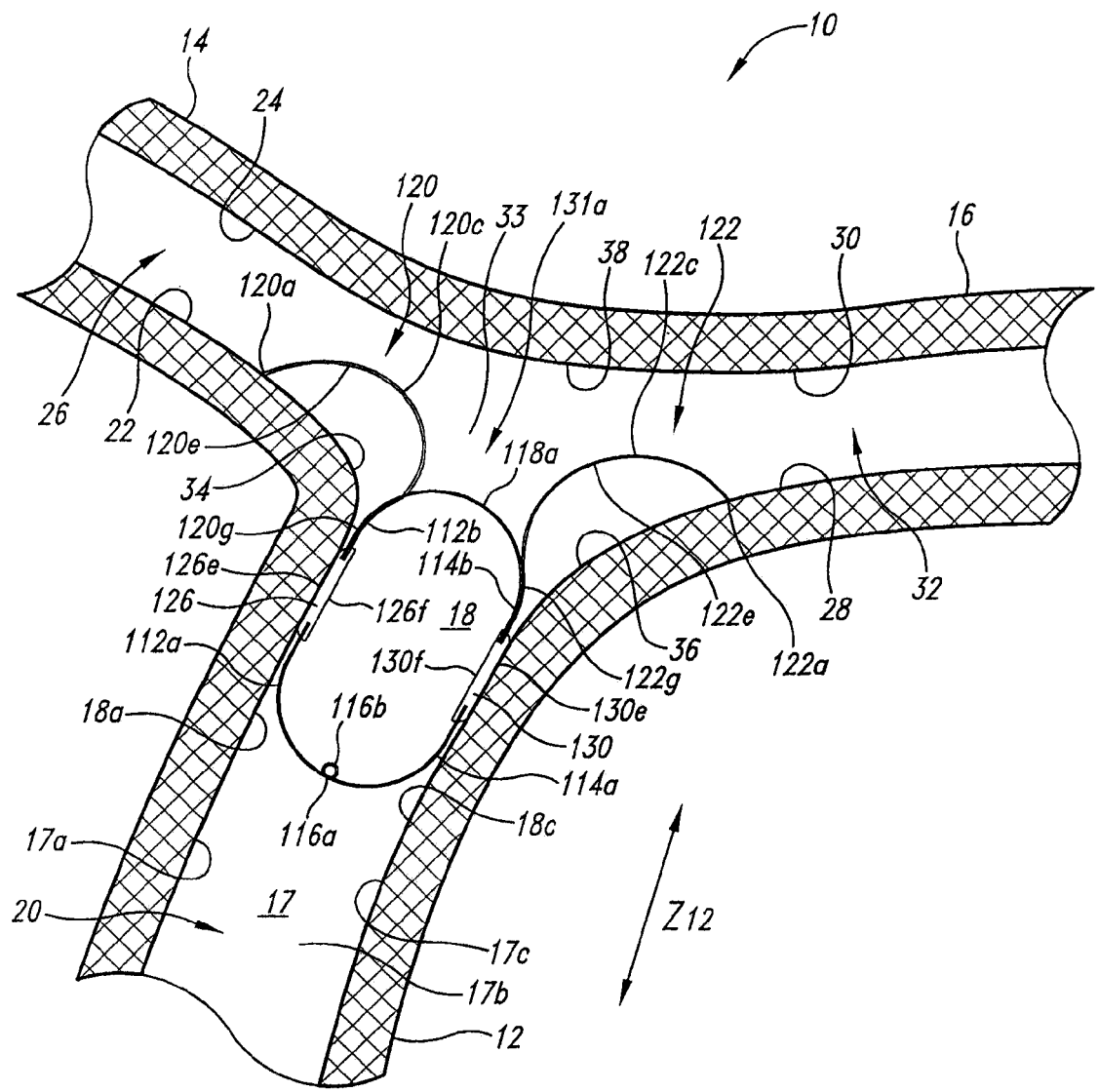
FIG. 24 is a front elevational view of the third vascular anchoring system and a fragmented sectional view of the bifurcated vasculature of FIG. 1 taken along the 1A-1A line with the third vascular anchoring system depicted as being inserted into the vascular trunk of the bifurcated vasculature.
Figure 25:
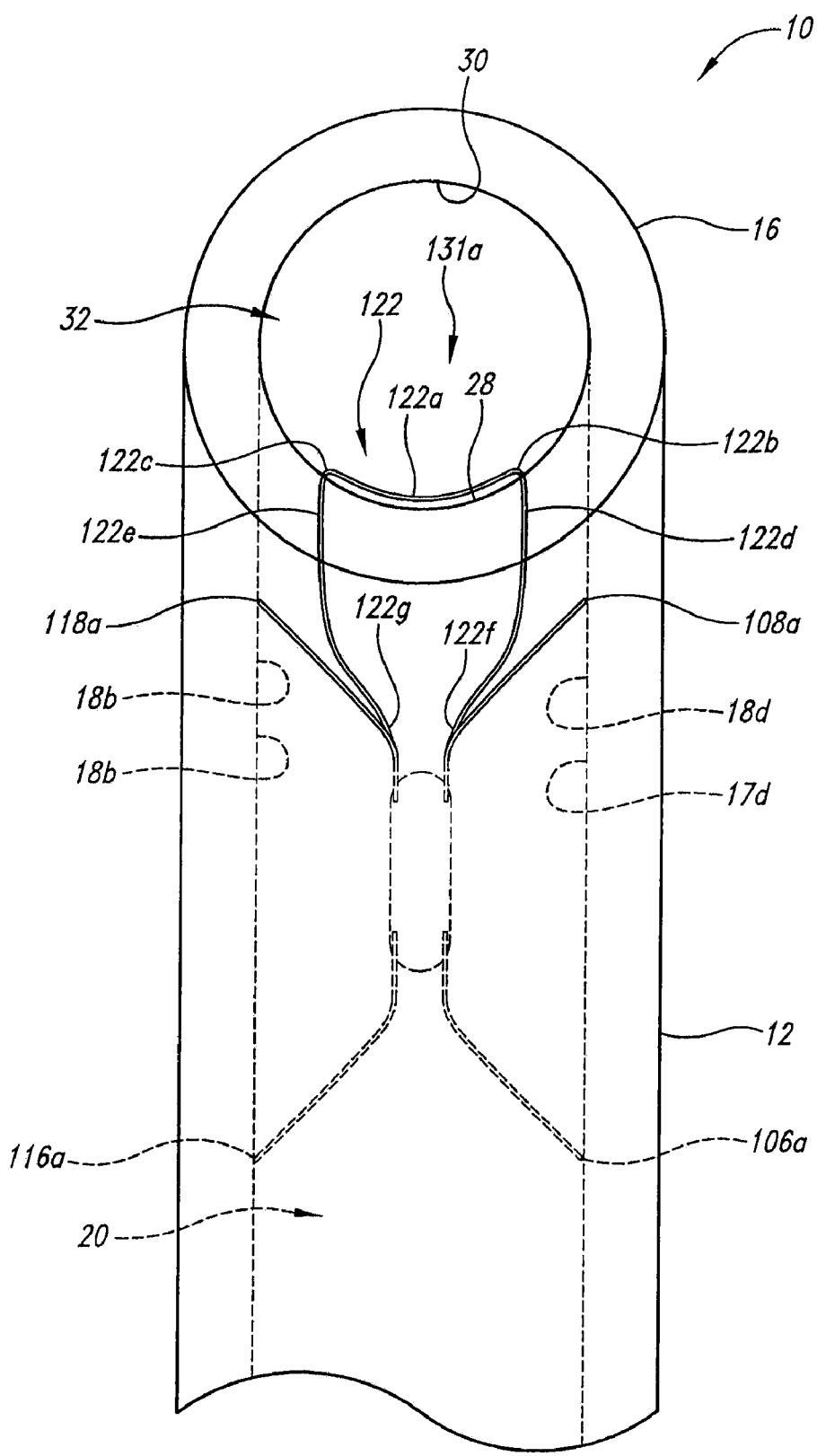
FIG. 25 is a side elevational view of the third vascular anchoring system and a fragmented sectional view of the bifurcated vasculature of FIG. 1 taken along the 15-15 line with the vascular anchoring system depicted as being inserted into the vascular trunk of the bifurcated vasculature.

The third vascular anchoring system 131 is shown in FIGS. 24 and 25 being located in a first position 131a within the bifurcated vasculature 10. Fluid flow in the bifurcated vasculature 10 does not substantially effect positioning of the third vascular anchoring system 131 so has not been depicted in FIG. 24, FIG. 25, and following. The first anchoring branch member 120 is located generally within the first branch interior 26 of the first vascular branch 14. The saddle end portion 120a and parts of the first saddle side portion 120b and the second saddle side portion 120c of the saddle frame portion 120h of the second anchoring branch member 120 is adjacent the first branch proximate surface 22 of the first vascular branch 14.

In the first position 131a of the third vascular anchoring system 131, the third anchoring trunk member 128 is located in the first position 128a. The first anchoring branch member 120 is located generally within the first branch interior 26 of the first vascular branch 14. The saddle end portion 120a and parts of the first saddle side portion 120b and the second saddle side portion 120c of the saddle frame portion 120h of the second anchoring branch member 120 is adjacent the first branch proximate surface 22 of the first vascular branch 14.

The second anchoring branch member 122 is located generally within the second branch interior 32 of the second vascular branch 16. The saddle end portion 122a and parts of the first saddle side portion 122b and the second saddle side portion 122c of the saddle frame portion 122h of the second anchoring branch member 122 is adjacent the second branch proximate surface 28 of the second vascular branch 16.

Figure 26:
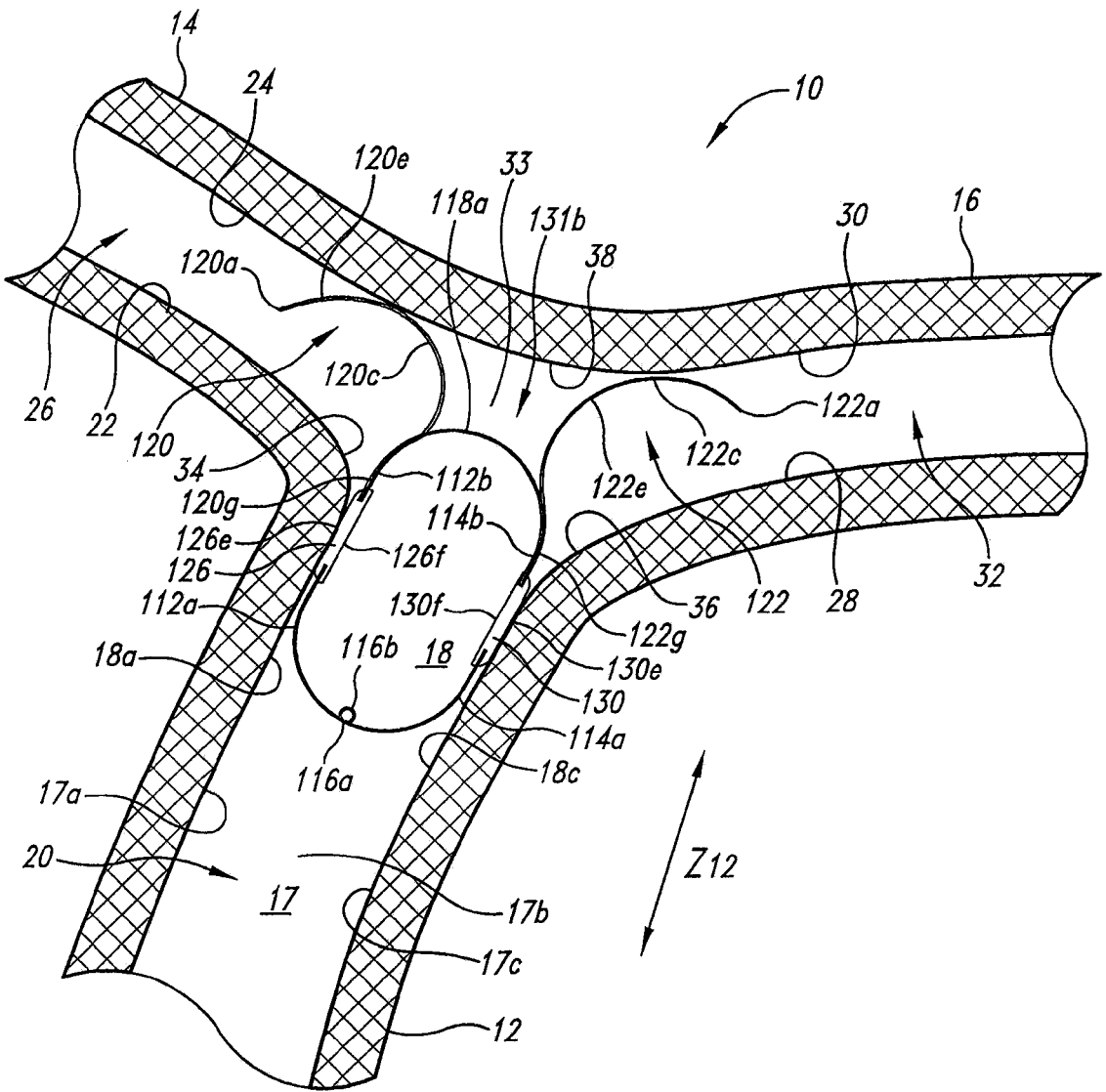
FIG. 26 is a front elevational view of the third vascular anchoring system and a fragmented sectional view of the bifurcated vasculature of FIG. 1 taken along the 1A-1A line with the third of the vascular anchoring system depicted as being inserted into the vascular trunk of the bifurcated vasculature.
Figure 27:
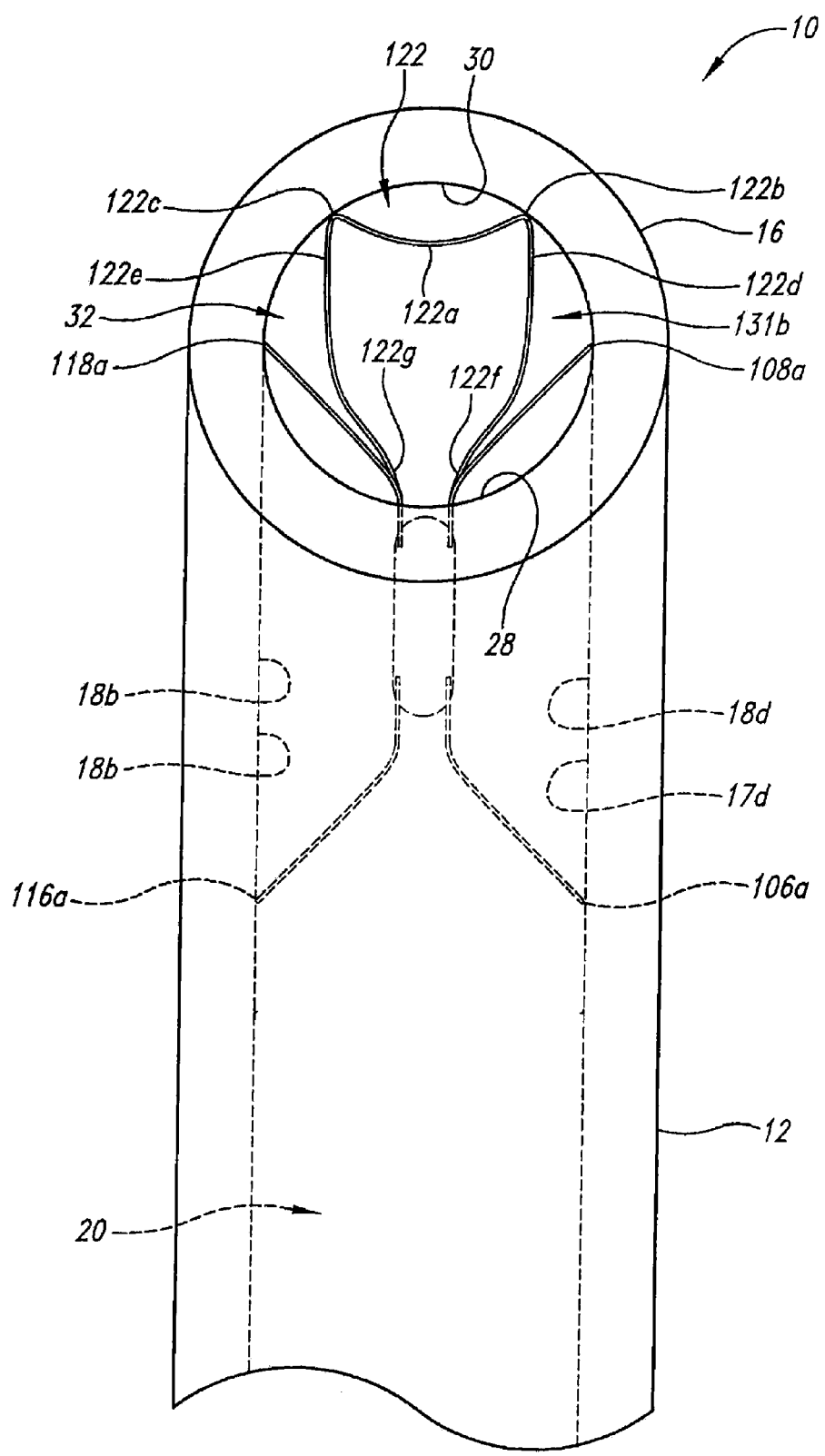
FIG. 27 is a side elevational view of the third vascular anchoring system and a fragmented sectional view of the bifurcated vasculature of FIG. 1 taken along the 15-15 line with the third of the vascular anchoring system depicted as being inserted into the vascular trunk of the bifurcated vasculature.

The third vascular anchoring system 131 is shown in FIGS. 26 and 27 as being located in a second position 131b within the bifurcated vasculature 10, which may be different than the first position 131a due to size differences between particular instances of the bifurcated vasculature 10 or size differences between particular instances of the first vascular anchoring system 131. In the second position 131b of the third vascular anchoring system 131, the third anchoring trunk member 128 is shifted slightly relative to the first position 128a to be partially positioned into the intersection 33 of the bifurcated vasculature 10. The first saddle side portion 120b and the second saddle side portion 120c of the first anchoring branch member 120 and the first saddle side portion 122b and the second saddle side portion 122c of the second anchoring branch member 122 are shown as touching the first branch distal surface 24 and the second branch distal surface 30, respectively.

Figure 28:
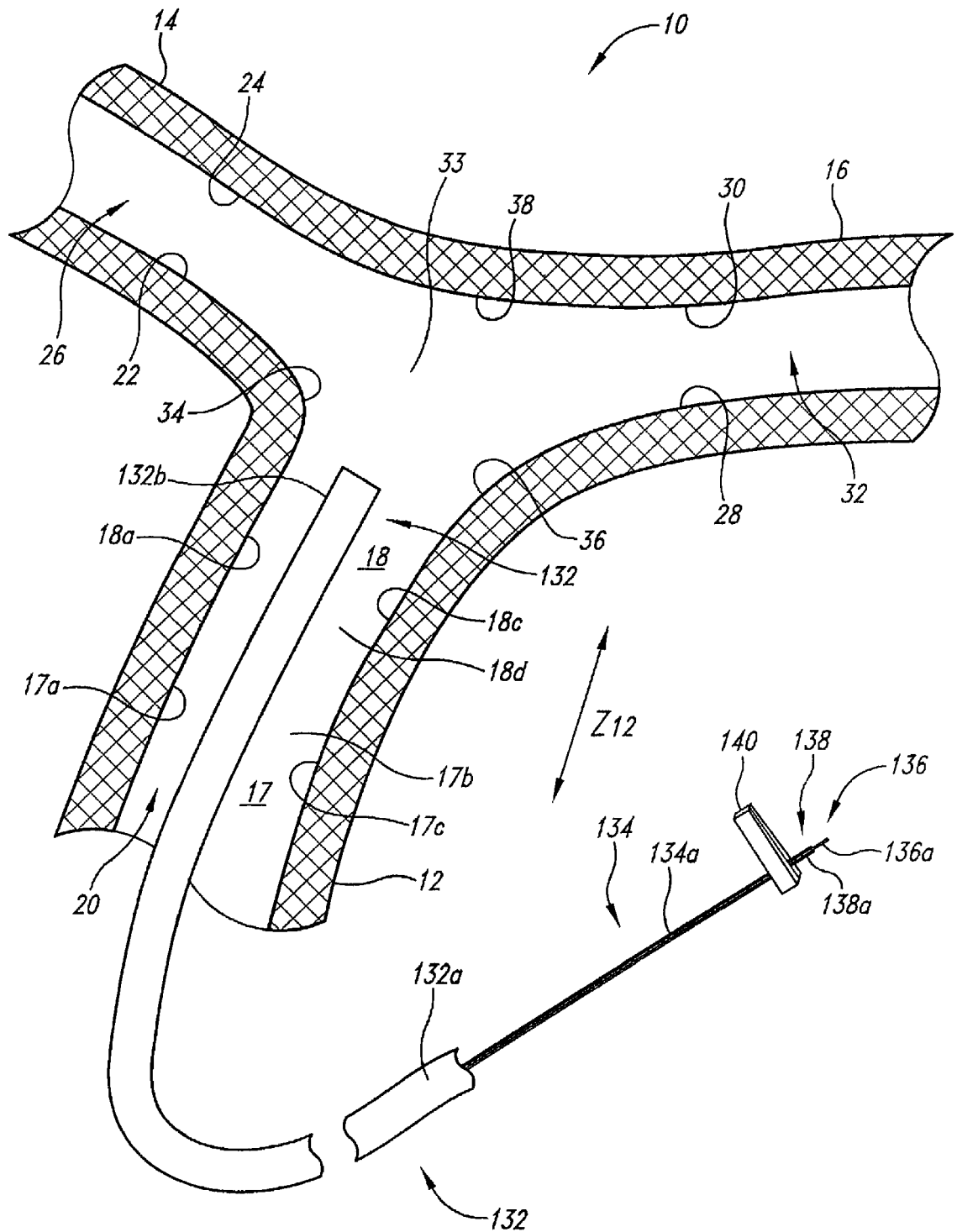
FIG. 28 is a sectional fragmented view of the bifurcated vasculature of FIG. 1 taken along the 1A-1A line and a front elevational fragmented view of a first catheter end external to the bifurcated vasculature with a first end of the deployment tether extending therefrom and a second catheter end inserted into the vascular trunk.

A catheter 132 with a first end 132a and a second end 132b is shown in FIG. 28 with the second end 132b being inserted into the vascular trunk 12 of the bifurcated vasculature 10. The first end 132a of the catheter 132 is shown with a first end 134a of a deployment tether 134 protruding therefrom. The deployment tether 134 includes a pinning member 136 with a first end 136a and a hooking member 138 with a first end 138a. The first end 136a of the pinning member 136 and the first end 138a of the hooking member 138 are depicted as comprising the first end 134a of the deployment tether 134. The pinning member 136 and the hooking member 138 can be made of a double-wire construction such as depicted. A clamp 140 or other device can be used to couple the pinning member 136 and the hooking member 138 together, as shown, when the catheter 132 is being inserted into the vascular trunk 12. Aspects include that the pinning member 136 and the hooking member 138 function to provide the operator with complete control over the axial and roll positions of the vascular anchoring system relative to the catheter tip 132b. The catheter tip 132b provides yaw and pitch control of the vascular anchoring system relative to the catheter 132 axis. The combined degree of control over the vascular anchoring system results in a deployment that is largely unaffected by the blood flowing past the device in the vascular trunk 12.

Figure 29:
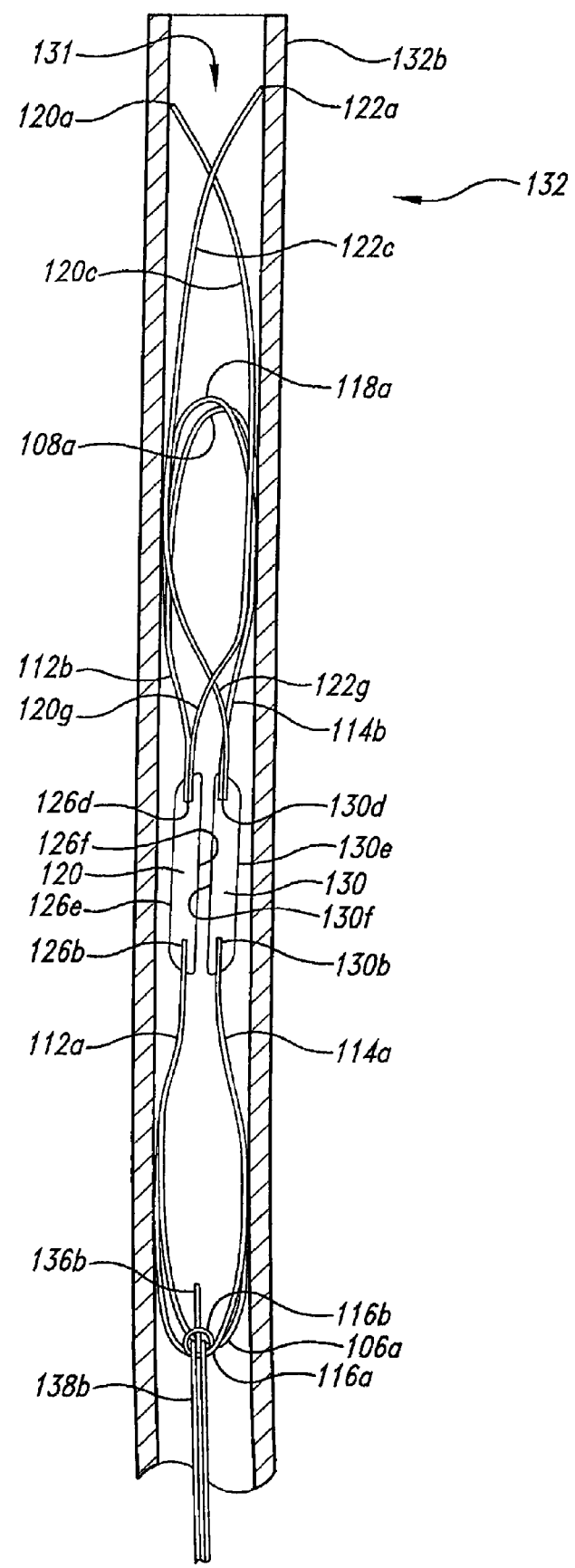
FIG. 29 is a sectional view of the second catheter end and a front elevational view of the third vascular anchoring system coupled with a second end of the deployment tether shown as inserted into the second catheter end.

A second end 134b of the deployment tether 134 is shown inside a portion of the catheter 132 at the second end 132b in FIG. 29 as having a second end 136b of the pinning member 136 and a second end 138b of the hooking member 138, which are depicted to couple with the third vascular anchoring system 131. Although the third vascular anchoring system 131 is depicted as being deployed by the catheter 132, the catheter 132 can similarly deploy other versions, such as the first vascular anchoring system 121 and the second vascular anchoring system 127.

Once the catheter 132 is positioned inside of the vascular trunk 12, the third vascular anchoring system 131 can be deployed into the bifurcated vasculature 10. A partial stage of deployment is shown in FIG. 30 having the first end 134a of the deployment tether 134 being pushed a first amount into the first catheter end 132a resulting in the first anchoring branch member 120 and the second anchoring branch member 122 being fully extended and the third anchoring trunk member 128 partially extended from the second catheter end 132b into the vascular trunk 12. The third vascular anchoring system 131 is shown in FIGS. 31 and 32 as being further deployed by the first end 134a of the deployment tether 134 being pushed a second amount greater than the first amount into the first catheter end 132a resulting in further extending of the third vascular anchoring system 131 from the second catheter end 132b with portions of the first component package 124 and the second component package 129 having exited from the catheter 132.

The third vascular anchoring system 131 is shown in FIGS. 33-35 as being further deployed by the first end 134a of the deployment tether 134 being pushed a third amount greater than the second amount into the first catheter end 132*a* resulting in the third vascular anchoring system 131 being fully extended from the second catheter end 132*b* into the bifurcated vasculature 10. FIG. 35 also better shows the second end 136*b* of the hooking member 136 having a hook 138*c* with an eyelet 138*d* that the second end 136*b* of the pinning member 136 extends therethrough to couple the second end of the pinning member to the second end of the hooking member thereby locking the coupling of the hook of the hooking member with the loop 116*b* of the first convex arch 116 of the second trunk section 110 of the third anchoring trunk member 128 of the third vascular anchoring system 131.

Once the third vascular anchoring system 131 is fully extended from the catheter 132, the clamp 140 is opened thereby uncoupling the pinning member 136 from the hooking member 138. The first end 136*a* of the pinning member 136 can then be pulled back away from the first end 132*a* of the catheter 132 thereby moving the second end 136*b* of the pinning member 136 out of the eyelet 138*d* of the hook 138*c* and unlocking the coupling of the hook with the loop as shown in FIG. 36. The hook 138*c* of the hooking member 138 can then be unhooked from the loop 116*b* of the third anchoring trunk member 128 to uncouple the third vascular anchoring system 131 from the deployment tether 134 as shown in FIG. 37. With the deployment tether 134 uncoupled from the third vascular anchoring system 131, the catheter 132 can be removed from the bifurcated vasculature 10 as shown in FIGS. 24-27.

An exemplary implementation of the third vascular anchoring system 131 is shown in FIG. 38 where the catheter 132 has been inserted into a pulmonary artery as the vascular trunk 12. The third vascular anchoring system 131 is shown engaging with the pulmonary artery as the vascular trunk 12, the left pulmonary artery of the heart as the first vascular branch 14 and the right pulmonary artery of the heart as the second vascular branch 16.

A first alternative implementation of the deployment tether 134 is shown being positioned inside of an alignment conduit 150, which includes a straight portion 152, a flex portion 154, and an engagement portion 156 having notches 158. In some implementations the straight portion 152 and the flex portion 154 are formed from a common tube in which a portion of the tube is further processed to result in the flex portion such as through molding, crumpling, or other. Alternatively, the flex portion 154 can be formed from a helical metal wire winding such as with 300 series stainless steel. The coil wire for implementations of the flex portion 154 can be round or flat depending upon the bending characteristics desired for the flex portion.

The engagement portion 156 can also be made from a stainless steel, such as 300 series stainless, and be joined to the flex portion by laser welding. The notches 158, better shown in FIG. 40, are used to engage the engagement portion 156 of the alignment conduit 150 with the third anchoring trunk member 128 as shown in FIG. 41. Before engagement of the notches 158 with the third anchoring trunk member 128, some versions of the flex portion 154 can be rather limp, but with engagement, a certain amount of rigidity is imparted by the deployment tether 134 to the alignment conduit 150 in general and the flex portion in particular so that anchoring trunk member can be rotated about an axis 159 positioned coaxial with the alignment conduit. The capability to rotate the third anchoring trunk member 128 about the axis 159 can assist in properly placing the third anchoring member inside of the bifurcated vasculature 10. Rotational alignment could be performed through the aid of visualization with fluoroscopy.

An alternative engagement portion 160 of the alignment conduit 150 is shown in FIG. 42 to include a first aperture 162 with the pinning member 136 therethrough and a second aperture 164 with the hooking member 138 therethrough to provide engagement of the alignment conduit 150 with the third anchoring trunk member 128 when the deployment tether 134 is engaged with the third anchoring trunk member.

From the foregoing it will be appreciated that, although specific embodiments of the invention have been described herein for purposes of illustration, various modifications may be made without deviating from the spirit and scope of the invention. For instance, the members, sections, and portions of the vascular anchoring systems can be formed as a multipiece construction or as a single integrated piece construction. In some implementations, the vascular anchoring systems, including trunk member portions and tether portions, can be formed from a nitinol alloy wire as a wire frame structure whereas other implementations can use other metal alloys, polymeric materials, and/or radiopacifying material. If a radiopacifying material is used it can be from gold, platinum, silver, tantalum, iridium, rhodium, and mixtures and alloys thereof. In some implementations, the radiopacifying material is one component of a mixture containing a polymer. Uses of a radiopacifying material can include positioning a radiopaque marker band on a tether wire for identification and visualization of the tether wire through x-ray techniques.

It is know that the large arteries have two distinct interrelated major functions including a low resistance blood distribution conduit to the peripheral organs, named conduit function, and a smoothing of pressure and flow pulsatility, in order to transform it into an almost continuous arteriolo-capilary flow and pressure, named the buffer function. Implementations are made to be highly resilient and compliant to accommodate a wide range of sizes of patients without resorting to models of varying sizes and to allow for size change of the vasculature since the pulmonary artery distends significantly between systole and diastole due in part to the buffer function described above. Just as the vessel wall is compliant so that it can store some energy from the heart and then sustain blood flow between heart contractions, implementations are also highly compliant, so that it does not disrupt this normal function of the vessel wall.

If instead the vessel wall is made stiffer by implanting other than highly compliant implementations, it is possibly that a patient's heart disease may be made worse through implantation of the implementations because the heart will have to contract harder and faster to pump the same amount of blood with less sustained flow between contractions. In this sense implementations are a sort of opposite in a sense to a conventional stent since an objective of a stent is to hold a vessel open, a stent is not high compliant but instead rather stiff to eliminate a good portion of vessel wall motion. In contrast to a stent, each of the implementations is highly compliant to maintain normal motion and buffer function of a vessel in which the implementation is implant. Furthermore, some portions of the vascular anchoring systems were described as using arches; however, other shaped members can be used instead. As shown, in this expanded state, the trunk member of the anchoring system can have a clear bore that allows for free passage of catheters and other medical devices to be inserted into or through the vascular trunk. Accordingly, the invention is not limited except as by the appended claims.

The invention claimed is:

1. For a bifurcated vasculature having a vascular trunk dividing into a first vascular branch and a second vascular branch at a vascular intersection, a system comprising:

an elongated enclosure having a first end and a second end;
a branch member coupled to and extending away from the first end of the elongated enclosure;
an elongated member having a first end and a second end, the elongated member extending in juxtaposition with and spaced apart from the elongated enclosure;
a first trunk section including: a first shaped member coupled with the first end of the elongated enclosure and extending to and coupling with the first end of the elongated member, and a second shaped member coupled with the second end of the elongated enclosure and extending to and coupling with the second end of the elongated member, and
a second trunk section including: a first shaped member coupled with the first end of the elongated enclosure and extending to and coupling with the first end of the elongated member; and a second shaped member coupled with the second end of the elongated enclosure and extending to and coupling with the second end of the elongated member,
the elongated enclosure, the branch member, the elongated member, the first trunk section, and the second trunk section sized and coupled together to be inserted in the vascular trunk, the branch member sized to be inserted into the bifurcated vasculature for at least a portion of the branch member to contact a portion of the first vascular branch while the elongated enclosure, the elongated member, the first trunk section and the second trunk section are positioned in the vascular trunk;
wherein the elongated enclosure defines a continuous lateral dimension greater than a combined lateral dimension of the branch member, the first trunk section, and the second trunk section, and wherein the continuous lateral dimension is configured to engage a patient's vessel.

2. The system of claim 1, the first trunk section further including a first elongated member wherein the first shaped member of the first trunk section is coupled to the first end of the elongated enclosure through the first elongated member of the first trunk section and the second shaped member of the first trunk section is coupled to the second end of the elongated enclosure through the first elongated member of the first trunk section.

3. The system of claim 1 wherein the first trunk section, the second trunk section, the elongated member, and the branch member are of a one-piece construction.

4. The system of claim 1 wherein the first trunk section, the second trunk section, the elongated member, and the branch member are of a multi-piece construction.

5. The system of claim 1 wherein the first trunk, the second trunk section, the elongated member, and the branch member are of a nitinol metal alloy.

6. The system of claim 1 wherein the first trunk, the second trunk section, the elongated member, and the branch member of a polymeric material.

7. For a bifurcated vasculature having a vascular trunk dividing into a first vascular branch and a second vascular branch at a vascular intersection, a system comprising:
a first elongated enclosure having a first end and a second end;
a first branch member coupled to and extending away from the first end of the first elongated enclosure;
a second elongated enclosure having a first end and a second end, the second elongated enclosure extending with and spaced apart from the first elongated enclosure;
a second branch member coupled to and extending away from the first end of the second elongated enclosure;
a first trunk section including: a first shaped member coupled with the first end of the first elongated enclosure and extending to and coupling with the first end of the second elongated enclosure, and a second shaped member coupled with the second end of the first elongated enclosure and extending to and coupling with the second end of the second elongated member; and
a second trunk section including: a third shaped member coupled with the first end of the first elongated enclosure and extending to and coupling with the first end of the second elongated member; and a fourth shaped member coupled with the second end of the first elongated enclosure and extending to and coupling with the second end of the second elongated member, the first elongated enclosure, the second elongated enclosure, the first trunk section, and the second trunk section sized and coupled together to be inserted in the vascular trunk, the first branch member sized to be inserted into the bifurcated vasculature for at least a portion of the first branch member to contact a portion of the first vascular branch while the first elongated enclosure, the second elongated enclosure, the first trunk section and the second trunk section are positioned in the vascular trunk, the second branch member sized to be inserted into the bifurcated vasculature for at least a portion of the second branch member to contact a portion of the second vascular branch while the first elongated enclosure, the second elongated enclosure, the first trunk section and the second trunk section are positioned in the vascular trunk;
wherein each of the elongated enclosures define a continuous lateral dimension greater than a combined lateral dimension of the branch members, the first trunk section, and the second trunk section, and wherein the continuous lateral dimension is configured to engage a patient's vessel.

8. The system of claim 7, the first trunk section further including an elongated member wherein the first shaped member of the first trunk section is coupled to the first end of the first elongated enclosure through the elongated member and the second shaped member of the first trunk section is coupled to the second end of the first elongated enclosure through the elongated member.

9. The system of claim 7 wherein the first trunk section, the second trunk section, the first branch member, and the second branch member are of a one-piece construction.

10. The system of claim 7 wherein the first trunk section, the second trunk section, the first branch member, and the second branch member are of a multi-piece construction.

11. The system of claim 7 wherein the first trunk, the second trunk section, the first branch member, and the second branch member are of a nitinol metal alloy.

12. The system of claim 7 wherein the first trunk, the second trunk section, the first branch member, and the second branch member are formed of a polymeric material.

13. For a bifurcated vasculature having a vascular trunk dividing into a first vascular branch and a second vascular branch at a vascular intersection, a system comprising:
a first elongated enclosure;
a first branch member coupled to and extending away from the first elongated enclosure;
a second elongated enclosure, the second elongated enclosure extending in juxtaposition with and spaced apart from the first elongated enclosure;
a second branch member coupled to and extending away from the second elongated enclosure;

a first shaped member coupled with the first elongated enclosure and extending to and coupling with the second elongated enclosure; and a second shaped member coupled with the first elongated enclosure and extending to and coupling with the second elongated member, the first elongated enclosure, the second elongated enclosure, the first shaped member, and the second shaped member sized and coupled together to be inserted in the vascular trunk, the first branch member sized to be inserted into the bifurcated vasculature for at least a portion of the first branch member to contact a portion of the first vascular branch while the first elongated enclosure, the second elongated enclosure, the first shaped member section and the second shaped member are positioned in the vascular trunk, the second branch member sized to be inserted into the bifurcated vasculature for at least a portion of the second branch member to contact a portion of the second vascular branch while the first elongated enclosure, the second elongated enclosure, the first shaped member and the second shaped member are positioned in the vascular trunk; and wherein each of the elongated enclosures define a continuous lateral dimension greater than a combined lateral dimension of the branch members, the first shaped member, and the second shaped member, and wherein the continuous lateral dimension is configured to engage a patient's vessel.

14. The system of claim 13, further including an elongated member wherein the first shaped member is coupled to the first elongated enclosure through the elongated member and the second shaped member is coupled to the first elongated structure through the elongated member.

15. The system of claim 13 wherein the first shaped member, the second shaped member, the first branch member, and the second branch member are of a one-piece construction.

16. The system of claim 13 wherein the first shaped member, the second shaped member, the first branch member, and the second branch member are of a multi-piece construction.

17. The system of claim 13 wherein the first shaped member, the second shaped member, the first branch member, and the second branch member are of a nitinol metal alloy.

18. The system of claim 13 wherein the first shaped member, the second shaped member, the first branch member, and the second branch member of a polymeric material.

* * * * *